United States Patent [19]

Schuster et al.

[11] Patent Number: 5,792,851
[45] Date of Patent: Aug. 11, 1998

[54] HUMAN PROSTAGLANDIN TRANSPORTER

[75] Inventors: Victor L. Schuster, New York; Run Lu, Bronx, both of N.Y.

[73] Assignee: Albert Einstin College of Medicine of Yeshiva University, a Division of Yeshiva University, Bronx, N.Y.

[21] Appl. No.: 706,936

[22] Filed: Sep. 3, 1996

[51] Int. Cl.$^6$ .......................... C07H 21/04; C07K 16/28; C12N 15/12
[52] U.S. Cl. .................. 536/23.5; 435/69.1; 435/172.3; 435/320.1; 530/350; 530/388.2; 530/389.1; 530/391.3
[58] Field of Search .................... 536/23.5; 530/350, 530/388.2, 388.22, 389.1, 391.3; 435/320.1, 172.3, 69.1

[56] References Cited

PUBLICATIONS

Run Lu, Cloning, Tissue Expression and Functional Characterization of a Human Prostaglandin Transporter, J. Am. Soc. Nephrol. 6: 757, 1995 (Abstract) Presented at the American Society of Nephrology 28th Annual Meeting, San Diego, CA, Nov. 8, 1995.

Kanai, et al., Identification and Characterization of a Prostaglandin Transporter, Science, 268: 866–69 (May 12, 1995).

Kanai, et al. OATP-2, A Novel Prostaglandin Transporter: Substrate and Inhibitor Specificities and Affiritis, J. Am Soc Nephrol. 5: 311 (1994) (Abstract).

Lu, R et al. J. Clin. Invest. 98(5): 1142–1149. Sep. 1996.

Johnstone, A et al. Immunology in Practice, Johnstoine and Thorpe, eds. Blackwell Scientific Publications, Oxford, UK., 1987.

Primary Examiner—David Saunders
Assistant Examiner—F. Pierre Vander Vegt
Attorney, Agent, or Firm—Amster, Rothstein & Ebenstein

[57] ABSTRACT

The present invention provides a purified and isolated nucleic acid encoding human prostaglandin transporter (hPGT). The present invention also provides a vector comprising a nucleic acid encoding human prostaglandin transporter (hPGT), a cell stably transformed with this vector, as well as a method for producing a recombinant, human prostaglandin transporter (hPGT). The present invention also provides a purified and isolated human prostaglandin transporter (hPGT), and an antibody immunoreactive with this protein. The present invention further provides a method for evaluating the uptake of a selected prostaglandin by cells expressing nucleic acid encoding human prostaglandin transporter (hPGT). Finally, the present invention provides a vector and an embryonic stem cell each of which comprises nucleic acid encoding a mutant human prostaglandin transporter (hPGT), a non-human transgenic animal whose germ and somatic cells contain nucleic acid encoding a mutant human prostaglandin transporter (hPGT) introduced into said animal, or an ancestor thereof, at an embryonic stage, as well as a method for producing the non-human, transgenic animal.

22 Claims, 10 Drawing Sheets

```
hPGT  MGLLPKLGVS  QGSDTSTSRA  GRCARSVFGN  IKVFVLCQGL  LQLCQLLYSA   50
rPGT  ....L.P.AR  ...G..SVPD  R..P....S.  .......H..  ..........   50 hPGT  YFKSSLTTIE  KRFGLSSSSS  GLISSLNEIS  NAILIIFVSY  FGSRVHRPRL  100
rPGT  ..........  ..........  ..........  ..T....I..  .....N...M  100 hPGT  IGIGGFLAA   GAFILTLPHF  LSEPYQYTLA  STGNNSRLQA  ELCQKHWQDL  150
rPGT  .....L...   ...V......  ........ST  TD..R.SF.T  D.....FGA.  150 hPGT  PPSKCHSTTQ  NPQKETSSMW  GLMVVAQLLA  GIGTVPIQPF  GISYVDDFSE  200
rPGT  ........VP  DTH.....L..  ..........  ..........  ........A.  200 hPGT  PSNSPLYISI  LFAISVFGPA  FGYLLGSIML  QIFVDYGRVN  TAAVNLVPGD  250
rPGT  .T........  ....A.....  ......V..   R........D  ..T...S...  250 hPGT  PRWIGAWWLG  LLISSALLVL  TSFPFFFFPR  AMPIGAKRAP  ATADEARKLE  300
rPGT  ..........  .....GF.IV  ..L.......  ..SR..E.-S  V..E.TMQT.  299 hPGT  EAKSRGSLVD  FIKRFPCIFL  RLLMNSLFVL  VVLAQCTFSS  VIAGLSTFLN  350
rPGT  .D......M.  ......R...  .....P..M.  ...S......  ..........  349 hPGT  KFLEKQYGTS  AAYANFLIGA  VNLPAAALGM  LFGGILMKRF  VFSLQTIPRI  400
rPGT  ........AT  ..........  ..........  ..........  ..P......V  399 hPGT  ATTIITISMI  LCVPLFFMGC  STPTVAEVYP  PSTSSSIHPQ  SP-ACRRDCS  449
rPGT  .A........  ..........  ..SA......  ..........  Q.P.......  449 hPGT  CPDSIFHPVC  GDNGIEYLSP  CHAGCSNIMM  SSATSKQLIY  LNCSCVTGGS  499
rPGT  ....F.....  ....V..V..  ......ST.T  ..EA..EP..  ......S...  499 hPGT  ASAKTGSCPV  PCAHFLLPAI  FLISFVSLIA  CISHNPLYMM  VLRVVNQEEK  549
rPGT  ..QDRLMPH.  LR.-L...S.  ......AA...  ..........  ......D..  548 hPGT  SFAIGVQFLL  MRLLAWLPSP  ALYGLTIDHS  CIRWNSLCLG  RRGACAYYDN  599
rPGT  ..........  .........A.  S....L..S.  .V...Y..S.  ..........  598 hPGT  DALRDRYLGL  QMGYKALGML  LLCFISWRVK  KNKEYNVQ-K  AAGLI        643
rPGT  ....N.....  ..V.....T.  ..F.....M.  ..R..SL.EN  TS...        643
```

FIG. 3B

Human PGT cDNA Sequence

| | | | | |
|---|---|---|---|---|
| AATTCCGGGT | CGCCTCTCAC | CCGCCCCGGC | CGCTCCAGCC | CGAGGCGCCC | 50
| CGACCCCGCG | CCACTCCGCG | CCCGGCCAGC | CGCCCGCAGC | CATGGGGCTC | 100
| CTGCCCAAGC | TCGGCGTGTC | CCAGGGCAGC | GACACCTCTA | CTAGCCGAGC | 150
| CGGCCGCTGT | GCCCGCTCGG | TCTTCGGCAA | CATTAAGGTG | TTTGTGCTCT | 200
| GCCAAGGCCT | CCTGCAGCTC | TGCCAACTCC | TGTACAGCGC | CTACTTCAAG | 250
| AGCAGCCTCA | CCACCATTGA | GAAGCGCTTT | GGGCTCTCCA | GTTCTTCATC | 300
| GGGTCTCATT | TCCAGCTTGA | ATGAGATCAG | CAATGCCATC | CTCATCATCT | 350
| TTGTCAGCTA | CTTTGGCAGC | CGGGTGCACC | GTCCACGTCT | GATTGGCATC | 400
| GGAGGTCTCT | TCCTGGCTGC | AGGTGCCTTC | ATCCTCACCC | TCCACACTT | 450
| CCTCTCCGAG | CCCTACCAGT | ACACCTTGGC | CAGCACTGGG | AACAACAGCC | 500
| GCTTGCAGGC | CGAGCTCTGC | CAGAAGCATT | GGCAGGACCT | GCCTCCCAGT | 550
| AAGTGCCACA | GCACCACCCA | GAACCCCAG | AAGGAGACCA | GCAGCATGTG | 600
| GGGCCTGATG | GTGGTTGCCC | AGCTGCTGGC | TGGCATCGGG | ACAGTGCCTA | 650
| TTCAGCCATT | TGGGATCTCC | TATGTGGATG | ACTTCTCAGA | GCCCAGCAAC | 700
| TCGCCCCTGT | ACATCTCCAT | CTTATTTGCC | ATCTCTGTAT | TTGGACCGGC | 750
| TTTCGGGTAC | CTGCTGGGCT | CTATCATGCT | GCAGATCTTT | GTGGACTATG | 800
| GCAGGGTCAA | CACAGCTGCA | GTTAACTTGG | TCCCGGGTGA | CCCCCGATGG | 850
| ATTGGAGCCT | GGTGGCTAGG | CCTGCTCATT | TCTTCAGCTT | TATTGGTTCT | 900
| CACCTCTTTC | CCCTTTTTT | TCTTCCCTCG | AGCAATGCCC | ATAGGAGCAA | 950
| AGAGGGCTCC | TGCCACAGCA | GATGAAGCAA | GGAAGTTGGA | GGAGGCCAAG | 1000
| TCAAGAGGCT | CCCTGGTGGA | TTTCATTAAA | CGGTTTCCAT | GCATCTTTCT | 1050
| GAGGCTCCTG | ATGAACTCAC | TCTTCGTCCT | GGTGGTCCTG | GCCCAGTGCA | 1100
| CCTTCTCCTC | CGTCATTGCT | GGCCTCTCA | CCTTCCTCAA | CAAGTTCCTG | 1150
| GAGAAGCAGT | ATGGCACCTC | AGCAGCCTAT | GCCAACTTCC | TCATTGGTGC | 1200
| TGTGAACCTC | CCTGCTGCAG | CCTTGGGGAT | GCTGTTTGGA | GGAATCCTCA | 1250
| TGAAGCGCTT | TGTTTTCTCT | CTACAAACCA | TTCCCCGCAT | AGCTACCACC | 1300
| ATCATCACCA | TCTCCATGAT | CCTTTGTGTT | CCTTTGTTCT | TCATGGGATG | 1350
| CTCCACCCCA | ACTGTGGCCG | AAGTCTACCC | CCCTAGCACA | TCAAGTTCTA | 1400
| TACATCCGCA | GTCTCCTGCC | TGCCGCAGGG | ACTGCTCGTG | CCCAGATTCT | 1450
| ATCTTCCACC | CGGTCTGTGG | AGACAATGGA | ATCGAGTACC | TCTCCCCTTG | 1500
| CCATGCCGGC | TGCAGCAACA | TCAACATGAG | CTCTGCAACC | TCCAAGCAAC | 1550
| TGATCTATTT | GAACTGCAGC | TGTGTGACCG | GGGGATCCGC | TTCAGCAAAG | 1600
| ACAGGATCGT | GCCCTGTCCC | CTGTGCCCAC | TTCCTGCTCC | CGGCCATCTT | 1650
| CCTCATCTCC | TTCGTGTCCC | TGATAGCCTG | CATCTCCCAC | AACCCCTCT | 1700
| ACATGATGGT | TCTGCGTGTG | GTGAACCAGG | AGGAAAAGTC | ATTTGCCATC | 1750
| GGGGTGCAGT | TCTTGTTGAT | GCGCTTGCTG | GCCTGGCTGC | CATCTCCAGC | 1800
| CCTCTATGGC | CTCACCATTG | ACCACTCCTG | CATCCGGTGG | AACTCGCTGT | 1850
| GCTTGGGGAG | GCGAGGGGCC | TGCGCCTACT | ATGACAACGA | TGCTCTCCGA | 1900
| GACAGGTACC | TGGGCCTGCA | GATGGGCTAC | AAGGCGCTGG | GCATGCTGCT | 1950
| GCTTTGCTTC | ATCAGCTGGA | GGGTGAAGAA | GAACAAGGAG | TACAACGTGC | 2000
| AGAAGGCGGC | AGGCCTCATC | TGACCCCACC | CTGGGCCACT | GCCTGCTCCA | 2050
| GAGAGTGGAC | CTTGACTCTT | CCACACCTGC | CTATACTCAC | TAATGTTAAC | 2100
| ACGTCATTTC | CTTTTGTAT | TTTTAAACAA | GAAAGAAAAC | CCCAGTCCTC | 2150
| ATTTGCCTTC | CCTACCTCTT | CCTCCCAGAG | TCCTCCCAC | AGTTCCTAAG | 2200
| GGCCACTGTG | TACCCGGGCT | GTGTGGGCCA | GAACTGGGGG | GCTGAGTCTT | 2250
| CCCTGGCCCC | TTGGAAGAGG | CCCCCAGATG | CCCAGGCTCA | CTTCAGTGTT | 2300
| GAGTCCTCCA | TTGAGGATGC | CCACTGAGGC | AGCCAGGCCC | CTCACCAGCC | 2350
| CTGGGGGGAA | TCCTAAACAG | AGAGAGAAAA | AGGGTATCTG | CCCTTCTTGC | 2400
| CAGGCAGCTC | CACTCTCCCG | CTGACTGCCC | ACACCCTGCA | GAGTGGCAGG | 2450
| GGTGAAAGGA | AGAAGGAAGT | GGCTGAGTTA | TTAATAGCCA | GAGCCACTGG | 2500

FIG. 7A

```
GAGACTGGGG AGACTGGCTG TAACCCCCTT CACACCTGGG TTTGGCATCA    2550
GCACAGACTA CGGGAGGGGC TGGCTCCCTC CCCCTCAGAC CCTCACTTCC    2600
TGTACCTAGA GGCCATTCTG GATGCTGCCA TGTTGGGAAG TACAGTCTCT    2650
GCCCATTACC TGCATGCAGG CACCAGAGCA GGGACTGAGA AACCCCAAGG    2700
ATGGGTCATC TAAGTGCTGT CCATATGAAC CCTGGACTTT CTGTCCTTAG    2750
ATCCTCACAT GTTATCCCTG TCTTTCTGGG GTACGTTTCA AACTGAGGAA    2800
GCTACAACAC AGTGAAGACC CAAGGAAGGC CTATGAAATG GTCCTGATGC    2850
CCAACCTCCC ACCCCTTCAA TGTGGGGACG AGACCCCTC ATCTCAGAGT     2900
AATGGGAAGA ACCTCCACA TCTCCCTGGC AGCAGATGAG GTGGCTTCAC     2950
ATGCACTTCC CTGTCTGGAC TTCAGCCCGT ATTCCGAGGA GTAGAGAGGC    3000
AGAAGAGATG TCAGCAAAGC AAGTGATGAA GCAGAGTGGA TGTCCACTGT    3050
CACCAAGCTG GATGGCAAGC TGCGGCCCAC AAAACAGCCA GTCAGGTTGG    3100
CTTTCCTGGT TTCAGACATG CTCATACCAT TCCCATTTTC TCAGCCTCTT    3150
CTCTGCCTCC AGAGAGGTGG ATGCCTGGGT TGAGAGACAC AGCTGCTACG    3200
TGATAGATGT TGAGAGACAG AAGCCAACGA AGGAGGTCAT TCATCAACAA    3250
ATATATTTAT TGGAGACCGA CTTTGTGCAA AGCAATGCTA ATCAGGGTTC    3300
TCCATGGAGC TTCCCTCAGC TCTTACCTCA CCTCCCTCCA TTTACATTAG    3350
GGCCTTCTCC CAGGGTGTGC TCGGTGGGCA GTGTGGGACT GGGGGTGTGG    3400
GAGTTGGTGA GAGCAGGAGG AGAGGTGGGG ACAGCAAGAA GCCACAGATT    3450
GGCATGAAGG ATCCTGACCT GACTATCCAT GCCATCCATG GCCCCAGAC     3500
TGACTCTGCA CCTGGCCCTT TGCCAGACAG CTCTGTCTCC CCATGTCCTC    3550
TGGAACAGCT GGGCATGGGT CATGGCCATT CATGACCCTT AAGTGCCACC    3600
CTTCTTGGAA GACCCCCTCC AGAAGCATAC TGGAAGCCAC CTCTGGAAAA    3650
GCCTCATATG GTGATATGCC AAAATATTTA TGTCAATGTC AAACAAAGT     3700
CCAATGCCAT GAGACTGAAG TCTTTGTGGA AACCACTGTT ACAGACAAGC    3750
TTATTTCCAA AGCCACCTCA TTTCCAAACA TCTCACTCAG GAAGGGAGGC    3800
TCAATGTAAC CTCAGGGGCC AGTTTTAGCA TTTGAAATGG TTCTGCTTGG    3850
AAAATGATGC CCTGCAACTA ACCCTGGTCT TTCCCATGGC AATTTAACCA    3900
CATTTGGAAG GCACTGCCTT CAGCTGAGTT TATGAACAAT GAATGCCAAC    3950
CTTCAGGTTC TAGAAGATTG GTTGCACTCC AAACCTTTA TTCTATTATA     4000
TTACTATTAA AATATTCTAA TTTTGCTATT GAGGTAAAAA AAAAAA        4046
```

FIG. 7B 5,792,851

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4046
        ( B ) TYPE: NUCLEIC ACID
        ( C ) STRANDEDNESS: DOUBLE
        ( D ) TOPOLOGY: LINEAR ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( A ) ORGANISM: HUMAN
        ( B ) INDIVIDUAL ISOLATE: PROSTAGLANDIN TRANSPORTER ( x i ) SEQUENCE DESCRIPTION: SEQ ID NO: 1:

```
AATTCCGGGT  CGCCTCTCAC  CCGCCCCGGC  CGCTCCAGCC  CGAGGCGCCC       50
CGACCCCGCG  CCACTCCGCG  CCCGGCCAGC  CGCCCGCAGC  CATGGGGCTC      100
CTGCCCAAGC  TCGGCGTGTC  CCAGGGCAGC  GACACCTCTA  CTAGCCGAGC      150
CGGCCGCTGT  GCCCGCTCGG  TCTTCGGCAA  CATTAAGGTG  TTTGTGCTCT      200
GCCAAGGCCT  CCTGCAGCTC  TGCCAACTCC  TGTACAGCGC  CTACTTCAAG      250
AGCAGCCTCA  CCACCATTGA  GAAGCGCTTT  GGGCTCTCCA  GTTCTTCATC      300
GGGTCTCATT  TCCAGCTTGA  ATGAGATCAG  CAATGCCATC  CTCATCATCT      350
TTGTCAGCTA  CTTTGGCAGC  CGGGTGCACC  GTCCACGTCT  GATTGGCATC      400
GGAGGTCTCT  TCCTGGCTGC  AGGTGCCTTC  ATCCTCACCC  TCCCACACTT      450
CCTCTCCGAG  CCCTACCAGT  ACACCTTGGC  CAGCACTGGG  AACAACAGCC      500
GCTTGCAGGC  CGAGCTCTGC  CAGAAGCATT  GGCAGGACCT  GCCTCCCAGT      550
AAGTGCCACA  GCACCACCCA  GAACCCCCAG  AAGGAGACCA  GCAGCATGTG      600
GGGCCTGATG  GTGGTTGCCC  AGCTGCTGGC  TGGCATCGGG  ACAGTGCCTA      650
TTCAGCCATT  TGGGATCTCC  TATGTGGATG  ACTTCTCAGA  GCCCAGCAAC      700
TCGCCCCTGT  ACATCTCCAT  CTTATTTGCC  ATCTCTGTAT  TTGGACCGGC      750
TTTCGGGTAC  CTGCTGGGCT  CTATCATGCT  GCAGATCTTT  GTGGACTATG      800
GCAGGGTCAA  CACAGCTGCA  GTTAACTTGG  TCCCGGGTGA  CCCCCGATGG      850
ATTGGAGCCT  GGTGGCTAGG  CCTGCTCATT  TCTTCAGCTT  TATTGGTTCT      900
CACCTCTTTC  CCCTTTTTTT  TCTTCCCTCG  AGCAATGCCC  ATAGGAGCAA      950
AGAGGGCTCC  TGCCACAGCA  GATGAAGCAA  GGAAGTTGGA  GGAGGCCAAG     1000
TCAAGAGGCT  CCCTGGTGGA  TTTCATTAAA  CGGTTTCCAT  GCATCTTTCT     1050
GAGGCTCCTG  ATGAACTCAC  TCTTCGTCCT  GGTGGTCCTG  GCCCAGTGCA     1100
CCTTCTCCTC  CGTCATTGCT  GGCCTCTCCA  CCTTCCTCAA  CAAGTTCCTG     1150
GAGAAGCAGT  ATGGCACCTC  AGCAGCCTAT  GCCAACTTCC  TCATTGGTGC     1200
TGTGAACCTC  CCTGCTGCAG  CCTTGGGGAT  GCTGTTTGGA  GGAATCCTCA     1250
TGAAGCGCTT  TGTTTCTCT   CTACAAACCA  TTCCCCGCAT  AGCTACCACC     1300
```

-continued

| | | | | | |
|---|---|---|---|---|---|
| ATCATCACCA | TCTCCATGAT | CCTTTGTGTT | CCTTTGTTCT | TCATGGGATG | 1350 |
| CTCCACCCCA | ACTGTGGCCG | AAGTCTACCC | CCCTAGCACA | TCAAGTTCTA | 1400 |
| TACATCCGCA | GTCTCCTGCC | TGCCGCAGGG | ACTGCTCGTG | CCCAGATTCT | 1450 |
| ATCTTCCACC | CGGTCTGTGG | AGACAATGGA | ATCGAGTACC | TCTCCCCTTG | 1500 |
| CCATGCCGGC | TGCAGCAACA | TCAACATGAG | CTCTGCAACC | TCCAAGCAAC | 1550 |
| TGATCTATTT | GAACTGCAGC | TGTGTGACCG | GGGGATCCGC | TTCAGCAAAG | 1600 |
| ACAGGATCGT | GCCCTGTCCC | CTGTGCCCAC | TTCCTGCTCC | CGGCCATCTT | 1650 |
| CCTCATCTCC | TTCGTGTCCC | TGATAGCCTG | CATCTCCAC | AACCCCCTCT | 1700 |
| ACATGATGGT | TCTGCGTGTG | GTGAACCAGG | AGGAAAAGTC | ATTTGCCATC | 1750 |
| GGGGTGCAGT | TCTTGTTGAT | GCGCTTGCTG | GCCTGGCTGC | CATCTCCAGC | 1800 |
| CCTCTATGGC | CTCACCATTG | ACCACTCCTG | CATCCGGTGG | AACTCGCTGT | 1850 |
| GCTTGGGGAG | GCGAGGGGCC | TGCGCCTACT | ATGACAACGA | TGCTCTCCGA | 1900 |
| GACAGGTACC | TGGGCCTGCA | GATGGGCTAC | AAGGCGCTGG | GCATGCTGCT | 1950 |
| GCTTTGCTTC | ATCAGCTGGA | GGGTGAAGAA | GAACAAGGAG | TACAACGTGC | 2000 |
| AGAAGGCGGC | AGGCCTCATC | TGACCCCACC | CTGGGCCACT | GCCTGCTCCA | 2050 |
| GAGAGTGGAC | CTTGACTCTT | CCACACCTGC | CTATACTCAC | TAATGTTAAC | 2100 |
| ACGTCATTTC | CTTTTTGTAT | TTTTAAACAA | GAAAGAAAAC | CCCAGTCCTC | 2150 |
| ATTTGCCTTC | CCTACCTCTT | CCTCCCAGAG | TCCTCCCCAC | AGTTCCTAAG | 2200 |
| GGCCACTGTG | TACCCGGGCT | GTGTGGGCCA | GAACTGGGGG | GCTGAGTCTT | 2250 |
| CCCTGGCCCC | TTGGAAGAGG | CCCCCAGATG | CCCAGGCTCA | CTTCAGTGTT | 2300 |
| GAGTCCTCCA | TTGAGGATGC | CCACTGAGGC | AGCCAGGCCC | CTCACCAGCC | 2350 |
| CTGGGGGGAA | TCCTAAACAG | AGAGAGAAAA | AGGGTATCTG | CCCTTCTTGC | 2400 |
| CAGGCAGCTC | CACTCTCCCG | CTGACTGCCC | ACACCCTGCA | GAGTGGCAGG | 2450 |
| GGTGAAAGGA | AGAAGGAAGT | GGCTGAGTTA | TTAATAGCCA | GAGCCACTGG | 2500 |
| GAGACTGGGG | AGACTGGCTG | TAACCCCCTT | CACACCTGGG | TTTGGCATCA | 2550 |
| GCACAGACTA | CGGGAGGGGC | TGGCTCCCTC | CCCCTCAGAC | CCTCACTTCC | 2600 |
| TGTACCTAGA | GGCCATTCTG | GATGCTGCCA | TGTTGGGAAG | TACAGTCTCT | 2650 |
| GCCCATTACC | TGCATGCAGG | CACCAGAGCA | GGGACTGAGA | AACCCCAAGG | 2700 |
| ATGGGTCATC | TAAGTGCTGT | CCATATGAAC | CCTGGACTTT | CTGTCCTTAG | 2750 |
| ATCCTCACAT | GTTATCCCTG | TCTTTCTGGG | GTACGTTTCA | AACTGAGGAA | 2800 |
| GCTACAACAC | AGTGAAGACC | CAAGGAAGGC | CTATGAAATG | GTCCTGATGC | 2850 |
| CCAACCTCCC | ACCCCTTCAA | TGTGGGGACG | AGACCCCTC | ATCTCAGAGT | 2900 |
| AATGGGAAGA | ACCTCCCACA | TCTCCCTGGC | AGCAGATGAG | GTGGCTTCAC | 2950 |
| ATGCACTTCC | CTGTCTGGAC | TTCAGCCCGT | ATTCCGAGGA | GTAGAGAGGC | 3000 |
| AGAAGAGATG | TCAGCAAAGC | AAGTGATGAA | GCAGAGTGGA | TGTCCACTGT | 3050 |
| CACCAAGCTG | GATGGCAAGC | TGCGGCCCAC | AAAACAGCCA | GTCAGGTTGG | 3100 |
| CTTTCCTGGT | TTCAGACATG | CTCATACCAT | TCCCATTTTC | TCAGCCTCTT | 3150 |
| CTCTGCCTCC | AGAGAGGTGG | ATGCCTGGGT | TGAGAGACAC | AGCTGCTACG | 3200 |
| TGATAGATGT | TGAGAGACAG | AAGCCAACGA | AGGAGGTCAT | TCATCAACAA | 3250 |
| ATATATTTAT | TGGAGACCGA | CTTTGTGCAA | AGCAATGCTA | ATCAGGGTTC | 3300 |

| | | | | |
|---|---|---|---|---|
| TCCATGGAGC | TTCCCTCAGC | TCTTACCTCA | CCTCCCTCCA | TTTACATTAG | 3350 |
| GGCCTTCTCC | CAGGGTGTGC | TCGGTGGGCA | GTGTGGGACT | GGGGGTGTGG | 3400 |
| GAGTTGGTGA | GAGCAGGAGG | AGAGGTGGGG | ACAGCAAGAA | GCCACAGATT | 3450 |
| GGCATGAAGG | ATCCTGACCT | GACTATCCAT | GCCATCCATG | GCCCCAGAC | 3500 |
| TGACTCTGCA | CCTGGCCCTT | TGCCAGACAG | CTCTGTCTCC | CCATGTCCTC | 3550 |
| TGGAACAGCT | GGGCATGGGT | CATGGCCATT | CATGACCCTT | AAGTGCCACC | 3600 |
| CTTCTTGGAA | GACCCCCTCC | AGAAGCATAC | TGGAAGCCAC | CTCTGGAAAA | 3650 |
| GCCTCATATG | GTGATATGCC | AAAATATTTA | TGTCAATGTC | AAACAAAGT | 3700 |
| CCAATGCCAT | GAGACTGAAG | TCTTTGTGGA | AACCACTGTT | ACAGACAAGC | 3750 |
| TTATTCCAA | AGCCACCTCA | TTTCCAAACA | TCTCACTCAG | GAAGGGAGGC | 3800 |
| TCAATGTAAC | CTCAGGGGCC | AGTTTTAGCA | TTTGAAATGG | TTCTGCTTGG | 3850 |
| AAAATGATGC | CCTGCAACTA | ACCTGGTCT | TTCCCATGGC | AATTTAACCA | 3900 |
| CATTGGAAG | GCACTGCCTT | CAGCTGAGTT | TATGAACAAT | GAATGCCAAC | 3950 |
| CTTCAGGTTC | TAGAAGATTG | GTTGCACTCC | CAAACCTTTA | TTCTATTATA | 4000 |
| TTACTATTAA | AATATTCTAA | TTTTGCTATT | GAGGTAAAAA | AAAAAA | 4046 |

( 2 ) INFORMATION FOR SEQ ID NO:2:

( i ) SEQUENCE CHARACTERISTICS:
        ( A ) LENGTH: 642
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: YES ( v i ) ORIGINAL SOURCE:
        ( A ) ORGANISM: HUMAN
        ( B ) INDIVIDUAL ISOLATE: PROSTAGLANDIN TRANSPORTER ( x i ) SEQUENCE DESCRIPTION: SEQ ID NO: 2:

```
Met  Gly  Leu  Leu  Pro  Lys  Leu  Gly  Val  Ser  Gln  Gly  Ser  Asp  Thr
 1                 5                    10                       15

Ser  Thr  Ser  Arg  Ala  Gly  Arg  Cys  Ala  Arg  Ser  Val  Phe  Gly  Asn
                  20                    25                       30

Ile  Lys  Val  Phe  Val  Leu  Cys  Gln  Gly  Leu  Leu  Gln  Leu  Cys  Gln
                  35                    40                       45

Leu  Leu  Tyr  Ser  Ala  Tyr  Phe  Lys  Ser  Ser  Leu  Thr  Thr  Ile  Glu
                  50                    55                       60

Lys  Arg  Phe  Gly  Leu  Ser  Ser  Ser  Ser  Gly  Leu  Ile  Ser  Ser
                  65                    70                       75

Leu  Asn  Glu  Ile  Ser  Asn  Ala  Ile  Leu  Ile  Ile  Phe  Val  Ser  Tyr
                  80                    85                       90

Phe  Gly  Ser  Arg  Val  His  Arg  Pro  Arg  Leu  Ile  Gly  Ile  Gly  Gly
                  95                    100                      105

Phe  Leu  Ala  Ala  Gly  Ala  Phe  Ile  Leu  Thr  Leu  Pro  His  Phe  Leu
                  110                   115                      120

Ser  Glu  Pro  Tyr  Gln  Tyr  Thr  Leu  Ala  Ser  Thr  Gly  Asn  Asn  Ser
                  125                   130                      135

Arg  Leu  Gln  Ala  Glu  Leu  Cys  Gln  Lys  His  Trp  Gln  Asp  Leu  Pro
                  140                   145                      150
```

-continued

| | | | | | | | | | | | | |
|---|---|---|---|---|---|---|---|---|---|---|---|---|
| Pro | Ser | Lys | Cys | His 155 | Ser | Thr | Thr | Gln | Asn 160 | Pro | Gln | Lys | Glu | Thr 165 |
| Ser | Ser | Met | Trp | Gly 170 | Leu | Met | Val | Val | Ala 175 | Gln | Leu | Leu | Ala | Gly 180 |
| Ile | Gly | Thr | Val | Pro 185 | Ile | Gln | Pro | Phe | Gly 190 | Ile | Ser | Tyr | Val | Asp 195 |
| Asp | Phe | Ser | Glu | Pro 200 | Ser | Asn | Ser | Pro | Leu 205 | Tyr | Ile | Ser | Ile | Leu 210 |
| Phe | Ala | Ile | Ser | Val 215 | Phe | Gly | Pro | Ala | Phe 220 | Gly | Tyr | Leu | Leu | Gly 225 |
| Ser | Ile | Met | Leu | Gln 230 | Ile | Phe | Val | Asp | Tyr 235 | Gly | Arg | Val | Asn | Thr 240 |
| Ala | Ala | Val | Asn | Leu 245 | Val | Pro | Gly | Asp | Pro 250 | Arg | Trp | Ile | Gly | Ala 255 |
| Trp | Trp | Leu | Gly | Leu 260 | Leu | Ile | Ser | Ser | Ala 265 | Leu | Leu | Val | Leu | Thr 270 |
| Ser | Phe | Pro | Phe | Phe 275 | Phe | Phe | Pro | Arg | Ala 280 | Met | Pro | Ile | Gly | Ala 285 |
| Lys | Arg | Ala | Pro | Ala 290 | Thr | Ala | Asp | Glu | Ala 295 | Arg | Lys | Leu | Glu | Glu 300 |
| Ala | Lys | Ser | Arg | Gly 305 | Ser | Leu | Val | Asp | Phe 310 | Ile | Lys | Arg | Phe | Pro 315 |
| Cys | Ile | Phe | Leu | Arg 320 | Leu | Leu | Met | Asn | Ser 325 | Leu | Phe | Val | Leu | Val 330 |
| Val | Leu | Ala | Gln | Cys 335 | Thr | Phe | Ser | Ser | Val 340 | Ile | Ala | Gly | Leu | Ser 345 |
| Thr | Phe | Leu | Asn | Lys 350 | Phe | Leu | Glu | Lys | Gln 355 | Tyr | Gly | Thr | Ser | Ala 360 |
| Ala | Tyr | Ala | Asn | Phe 365 | Leu | Ile | Gly | Ala | Val 370 | Asn | Leu | Pro | Ala | Ala 375 |
| Ala | Leu | Gly | Met | Leu 380 | Phe | Gly | Gly | Ile | Leu 385 | Met | Lys | Arg | Phe | Val 390 |
| Phe | Ser | Leu | Gln | Thr 395 | Ile | Pro | Arg | Ile | Ala 400 | Thr | Thr | Ile | Ile | Thr 405 |
| Ile | Ser | Met | Ile | Leu 410 | Cys | Val | Pro | Leu | Phe 415 | Phe | Met | Gly | Cys | Ser 420 |
| Thr | Pro | Thr | Val | Ala 425 | Glu | Val | Tyr | Pro | Pro 430 | Ser | Thr | Ser | Ser | Ser 435 |
| Ile | His | Pro | Gln | Ser 440 | Pro | Ala | Cys | Arg | Arg 445 | Asp | Cys | Ser | Cys | Pro 450 |
| Asp | Ser | Ile | Phe | His 455 | Pro | Val | Cys | Gly | Asp 460 | Asn | Gly | Ile | Glu | Tyr 465 |
| Leu | Ser | Pro | Cys | His 470 | Ala | Gly | Cys | Ser | Asn 475 | Ile | Asn | Met | Ser | Ser 480 |
| Ala | Thr | Ser | Lys | Gln 485 | Leu | Ile | Tyr | Leu | Asn 490 | Cys | Ser | Cys | Val | Thr 495 |
| Gly | Gly | Ser | Ala | Ser 500 | Ala | Lys | Thr | Gly | Ser 505 | Cys | Pro | Val | Pro | Cys 510 |
| Ala | His | Phe | Leu | Leu 515 | Pro | Ala | Ile | Phe | Leu 520 | Ile | Ser | Phe | Val | Ser 525 |
| Leu | Ile | Ala | Cys | Ile 530 | Ser | His | Asn | Pro | Leu 535 | Tyr | Met | Met | Val | Leu 540 |
| Arg | Val | Val | Asn | Gln 545 | Glu | Glu | Lys | Ser | Phe 550 | Ala | Ile | Gly | Val | Gln 555 |

```
Phe  Leu  Leu  Met  Arg  Leu  Leu  Ala  Trp  Leu  Pro  Ser  Pro  Ala  Leu
                    560                      565                      570

Tyr  Gly  Leu  Thr  Ile  Asp  His  Ser  Cys  Ile  Arg  Trp  Asn  Ser  Leu
                    575                      580                      585

Cys  Leu  Gly  Arg  Arg  Gly  Ala  Cys  Ala  Tyr  Tyr  Asp  Asn  Asp  Ala
                    590                      595                      600

Leu  Arg  Asp  Arg  Tyr  Leu  Gly  Leu  Gln  Met  Gly  Tyr  Lys  Ala  Leu
                    605                      610                      615

Gly  Met  Leu  Leu  Leu  Cys  Phe  Ile  Ser  Trp  Arg  Val  Lys  Lys  Asn
                    620                      625                      630

Lys  Glu  Tyr  Asn  Val  Gln  Lys  Ala  Ala  Gly  Leu  Ile
                    635                      640
```

( 2 ) INFORMATION FOR SEQ ID NO:3:

( i ) SEQUENCE CHARACTERISTICS:
        ( A ) LENGTH: 642
        ( B ) TYPE: AMINO ACID
        ( D ) TOPOLOGY: UNKNOWN ( i i ) MOLECULE TYPE:
        ( A ) DESCRIPTION: PROTEIN ( i i i ) HYPOTHETICAL: YES ( v i ) ORIGINAL SOURCE:
        ( A ) ORGANISM: RAT
        ( B ) INDIVIDUAL ISOLATE: PROSTAGLANDIN TRANSPORTER ( x i ) SEQUENCE DESCRIPTION: SEQ ID NO: 3:

```
Met  Gly  Leu  Leu  Leu  Lys  Pro  Gly  Ala  Arg  Gln  Gly  Ser  Gly  Thr
 1                   5                       10                      15

Ser  Ser  Val  Pro  Asp  Arg  Arg  Cys  Pro  Arg  Ser  Val  Phe  Ser  Asn
                    20                       25                      30

Ile  Lys  Val  Phe  Val  Leu  Cys  His  Gly  Leu  Leu  Gln  Leu  Cys  Gln
                    35                       40                      45

Leu  Leu  Tyr  Ser  Ala  Tyr  Phe  Lys  Ser  Ser  Leu  Thr  Thr  Ile  Glu
                    50                       55                      60

Lys  Arg  Phe  Gly  Leu  Ser  Ser  Ser  Ser  Ser  Gly  Leu  Ile  Ser  Ser
                    65                       70                      75

Leu  Asn  Glu  Ile  Ser  Asn  Ala  Thr  Leu  Ile  Ile  Phe  Ile  Ser  Tyr
                    80                       85                      90

Phe  Gly  Ser  Arg  Val  Asn  Arg  Pro  Arg  Met  Ile  Gly  Ile  Gly  Gly
                    95                       100                     105

Leu  Leu  Ala  Ala  Gly  Ala  Phe  Val  Leu  Thr  Leu  Pro  His  Phe  Leu
                    110                      115                     120

Ser  Glu  Pro  Tyr  Gln  Tyr  Thr  Ser  Thr  Thr  Asp  Gly  Asn  Arg  Ser
                    125                      130                     135

Ser  Phe  Gln  Thr  Asp  Leu  Cys  Gln  Lys  His  Phe  Gly  Ala  Leu  Pro
                    140                      145                     150

Pro  Ser  Lys  Cys  His  Ser  Thr  Val  Pro  Asp  Thr  His  Lys  Glu  Thr
                    155                      160                     165

Ser  Ser  Leu  Trp  Gly  Leu  Met  Val  Val  Ala  Gln  Leu  Leu  Ala  Gly
                    170                      175                     180

Ile  Gly  Thr  Val  Pro  Ile  Gln  Pro  Phe  Gly  Ile  Ser  Tyr  Val  Asp
                    185                      190                     195

Asp  Phe  Ala  Glu  Pro  Thr  Asn  Ser  Pro  Leu  Tyr  Ile  Ser  Ile  Leu
                    200                      205                     210
```

-continued

| | | | | | | | | | | | | |
|---|---|---|---|---|---|---|---|---|---|---|---|---|
| Phe | Ala | Ile | Ala | Val 215 | Phe | Gly | Pro | Ala | Phe 220 | Gly | Tyr | Leu | Leu | Gly 225 |
| Ser | Val | Met | Leu | Arg 230 | Ile | Phe | Val | Asp | Tyr 235 | Gly | Arg | Val | Asp | Thr 240 |
| Ala | Thr | Val | Asn | Leu 245 | Ser | Pro | Gly | Asp | Pro 250 | Arg | Trp | Ile | Gly | Ala 255 |
| Trp | Trp | Leu | Gly | Leu 260 | Leu | Ile | Ser | Ser | Gly 265 | Phe | Leu | Ile | Val | Thr 270 |
| Ser | Leu | Pro | Phe | Phe 275 | Phe | Phe | Pro | Arg | Ala 280 | Met | Ser | Arg | Gly | Ala 285 |
| Glu | Arg | Ser | Val | Thr 290 | Ala | Glu | Glu | Thr | Met 295 | Gln | Thr | Glu | Glu | Asp 300 |
| Lys | Ser | Arg | Gly | Ser 305 | Leu | Met | Asp | Phe | Ile 310 | Lys | Arg | Phe | Pro | Arg 315 |
| Ile | Phe | Leu | Arg | Leu 320 | Leu | Met | Asn | Pro | Leu 325 | Phe | Met | Leu | Val | Val 330 |
| Leu | Ser | Gln | Cys | Thr 335 | Phe | Ser | Ser | Val | Ile 340 | Ala | Gly | Leu | Ser | Thr 345 |
| Phe | Leu | Asn | Lys | Phe 350 | Leu | Glu | Lys | Gln | Tyr 355 | Gly | Ala | Thr | Ala | Ala 360 |
| Tyr | Ala | Asn | Phe | Leu 365 | Ile | Gly | Ala | Val | Asn 370 | Leu | Pro | Ala | Ala | Ala 375 |
| Leu | Gly | Met | Leu | Phe 380 | Gly | Gly | Ile | Leu | Met 385 | Lys | Arg | Phe | Val | Phe 390 |
| Pro | Leu | Gln | Thr | Ile 395 | Pro | Arg | Val | Ala | Ala 400 | Thr | Ile | Ile | Thr | Ile 405 |
| Ser | Met | Ile | Leu | Cys 410 | Val | Pro | Leu | Phe | Phe 415 | Met | Gly | Cys | Ser | Thr 420 |
| Ser | Ala | Val | Ala | Glu 425 | Val | Tyr | Pro | Pro | Ser 430 | Thr | Ser | Ser | Ser | Ile 435 |
| His | Pro | Gln | Gln | Pro 440 | Pro | Ala | Cys | Arg | Arg 445 | Asp | Cys | Ser | Cys | Pro 450 |
| Asp | Ser | Phe | Phe | His 455 | Pro | Val | Cys | Gly | Asp 460 | Asn | Gly | Val | Glu | Tyr 465 |
| Val | Ser | Pro | Cys | His 470 | Ala | Gly | Cys | Ser | Ser 475 | Thr | Asn | Thr | Ser | Ser 480 |
| Glu | Ala | Ser | Lys | Glu 485 | Pro | Ile | Tyr | Leu | Asn 490 | Cys | Ser | Cys | Val | Ser 495 |
| Gly | Gly | Ser | Ala | Ser 500 | Gln | Asp | Arg | Leu | Met 505 | Pro | His | Val | Leu | Arg 510 |
| Ala | Leu | Leu | Leu | Pro 515 | Ser | Ile | Phe | Leu | Ile 520 | Ser | Phe | Ala | Ala | Leu 525 |
| Ile | Ala | Cys | Ile | Ser 530 | His | Asn | Pro | Leu | Tyr 535 | Met | Met | Val | Leu | Arg 540 |
| Val | Val | Asn | Gln | Asp 545 | Glu | Lys | Ser | Phe | Ala 550 | Ile | Gly | Val | Gln | Phe 555 |
| Leu | Leu | Met | Arg | Leu 560 | Leu | Ala | Trp | Leu | Pro 565 | Ala | Pro | Ser | Leu | Tyr 570 |
| Gly | Leu | Leu | Ile | Asp 575 | Ser | Ser | Cys | Val | Arg 580 | Trp | Asn | Tyr | Leu | Cys 585 |
| Ser | Gly | Arg | Arg | Gly 590 | Ala | Cys | Ala | Tyr | Tyr 595 | Asp | Asn | Asp | Ala | Leu 600 |
| Arg | Asn | Arg | Tyr | Leu 605 | Gly | Leu | Gln | Met | Val 610 | Tyr | Lys | Ala | Leu | Gly 615 |

-continued

| Thr | Leu | Leu | Leu | Phe 620 | Phe | Ile | Ser | Trp | Arg 625 | Met | Lys | Lys | Asn | Arg 630 |
| --- | --- | --- | --- | --- | --- | --- | --- | --- | --- | --- | --- | --- | --- | --- |
| Glu | Tyr | Ser | Leu | Gln 635 | Glu | Asn | Thr | Ser | Gly 640 | Leu | Ile | | | |

( 2 ) INFORMATION FOR SEQ ID NO:4:

( i ) SEQUENCE CHARACTERISTICS:
        ( A ) LENGTH: 20
        ( B ) TYPE: NUCLEIC ACID
        ( C ) STRANDEDNESS: DOUBLE
        ( D ) TOPOLOGY: UNKNOWN ( i i ) MOLECULE TYPE:
        ( A ) DESCRIPTION: OLIGONUCLEOTIDE ( i i i ) HYPOTHETICAL: NO ( i v ) ANTI-SENSE: NO ( v i ) ORIGINAL SOURCE:
        ( B ) INDIVIDUAL ISOLATE: UNKNOWN ( x i ) SEQUENCE DESCRIPTION: SEQ ID NO: 4:

TAGTTCTAGA TCGCGAGCGG 20

1
HUMAN PROSTAGLANDIN TRANSPORTER

STATEMENT OF GOVERNMENT INTEREST

This invention was made with government support under NIH Grant No. RO1-DK-49688. As such, the government has certain rights in this invention.

BACKGROUND OF THE INVENTION

Prostaglandins (PGs) play ubiquitous and vital pathophysiological and therapeutic roles in human health and various disease states, such as glaucoma; pregnancy, labor, delivery, and abortion; gastric protection and peptic ulcer formation; intestinal fluid secretion; liver protection and damage; airway resistance and asthma; blood pressure control; and modulation of inflammatory cells (1–15).

As charged organic anions at physiological pH (16,17), PGs traverse biological membranes poorly (18). Accordingly, PG transport is carrier-mediated in many diverse tissues, including the lung (19–22), choroid plexus (23–28), liver (29), anterior chamber of the eye (23–25,30), vagina and uterus (31–33), and placenta (34,35). The rat "PGT" cDNA has been cloned and is the first cloned carrier known to catalyze the transport of PGE and $PGF_{2\alpha}$ (36). Prior to the present invention, however, the cDNA encoding the human prostaglandin transporter (hPGT) had not been identified.

The present invention is based upon the discovery of the human prostaglandin transporter (hPGT) cDNA. The discovery of the human prostaglandin transporter (hPGT) cDNA will permit the evaluation of various prostaglandin analogues to determine their biological half-life, and potentially, the design of prostaglandin analogues that are not transported by human prostaglandin transporter (hPGT). Such analogues might be cleared from the body more slowly than those that are transported by human prostaglandin transporter (hPGT), resulting in increased biological half-life of these drugs.

SUMMARY OF THE INVENTION

The present invention provides a purified and isolated nucleic acid encoding human prostaglandin transporter (hPGT). The present invention also provides a vector comprising a nucleic acid encoding human prostaglandin transporter (hPGT), a cell stably transformed with this vector, as well as a method for producing a recombinant, human prostaglandin transporter (hPGT).

In addition, the present invention provides a purified and isolated human prostaglandin transporter (hPGT), and an antibody immunoreactive with this protein. The present invention also provides a method for evaluating the uptake of a selected prostaglandin by cells expressing nucleic acid encoding human prostaglandin transporter (hPGT) comprising the steps of: (a) expressing nucleic acid encoding human prostaglandin transporter (hPGT) in cells; (b) introducing the prostaglandin to the cells; and (c) evaluating the uptake of the prostaglandin by the cells.

Finally, the present invention provides a vector and an embryonic stem cell each of which comprises nucleic acid encoding a mutant human prostaglandin transporter (hPGT), a non-human transgenic animal whose germ and somatic cells contain nucleic acid encoding a mutant human prostaglandin transporter (hPGT) introduced into said animal, or an ancestor thereof, at an embryonic stage, as well as a method for producing the non-human, transgenic animal.

Additional objects of the invention will be apparent from the description which follows.

2
BRIEF DESCRIPTION OF THE FIGURES

FIG. 3B represents the deduced amino acid sequence of hPGT compared with that of rat PGT. Dots in the hPGT sequence represent identity to rat PGT. Underlines: putative membrane-spanning domains. Black circles: charged residues within putative membrane spans that are conserved between hPGT, rat PGT, and the related transporter "oatp" (50).

Figure 4A:
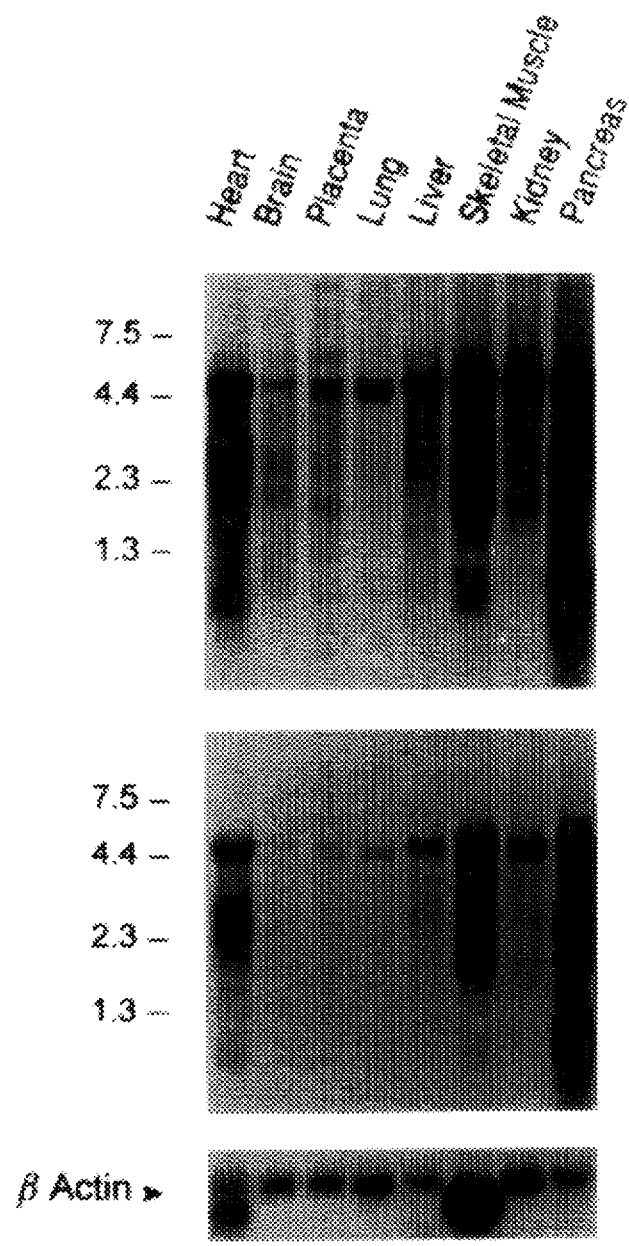

FIGS. 4A and B represent the Northern blot hybridization of human poly A+ RNA using a human PGT clone 3 anti-sense RNA probe. Hybridization and washing conditions as per Methods. Top panels represent exposure overnight, middle panels represent exposure for 15 minutes.

Figure 5:
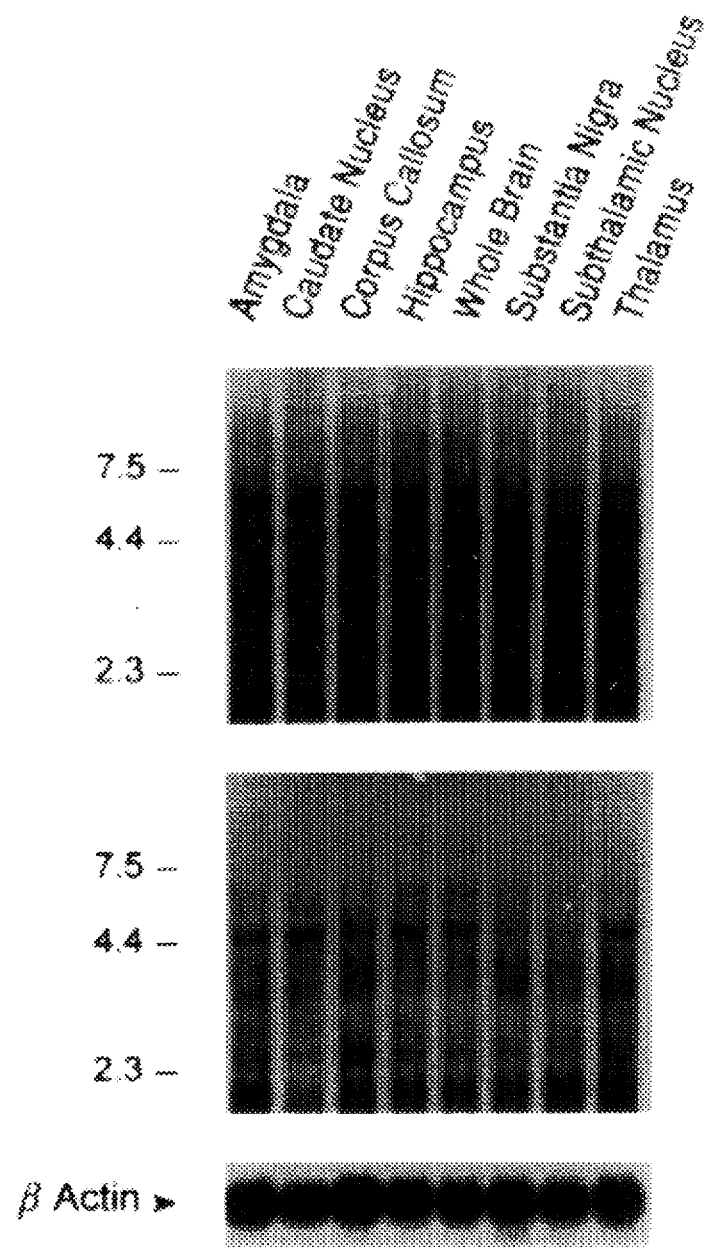

FIG. 5 represents the Northern blot hybridization of human brain poly A+ RNA using a human PGT clone 3 anti-sense RNA probe. Hybridization and washing conditions are as per FIGS. 4A and B. Top panels represent exposure for 1 hr, middle panels represent exposure for 5 minutes.

Figure 6:
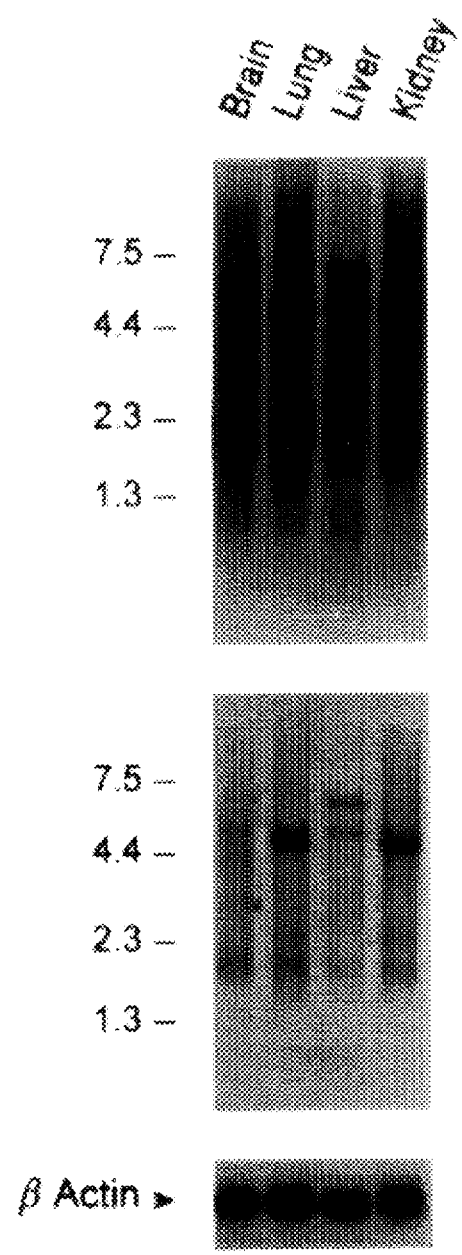

FIG. 6 represents the Northern blot hybridization of human fetal poly A+ RNA using a human PGT clone 3 anti-sense RNA probe. Hybridization and washing conditions, and film exposures are as per FIGS. 4A and B.

FIGS. 7A and 7B represent the nucleotide sequence for the human prostaglandin transporter (hPGT) cDNA.

DETAILED DESCRIPTION OF THE INVENTION

The present invention provides a purified and isolated nucleic acid encoding human prostaglandin transporter (hPGT). As used herein, the "nucleic acid" may be genomic DNA, cDNA or RNA, and includes the wild type gene which expresses the active gene product, including degenerate forms. In the preferred embodiment, the nucleic acid encodes the amino acid sequence of the human prostaglandin transporter (hPGT) contained in FIG. 3B, and most preferably, the nucleic acid has the nucleotide sequence contained in FIG. 7.

The present invention also provides single-stranded nucleic acid probes and mixtures thereof for use in detecting and/or isolating nucleic acid encoding the human prostaglandin transporter (hPGT). The nucleic acid probes may be prepared from the nucleic acid encoding the human prostaglandin transporter (hPGT), and includes complementary strands of this nucleic acid. The probes may be the full length sequence of the nucleic acid encoding the human prostaglandin transporter (hPGT), or fragments thereof. Typical probes are 12 to 40 nucleotides in length. Generally, the probes are complementary to the coding sequence, although probes to introns are also contemplated. The probes may be synthesized using an oligonucleotide synthesizer such as Applied Biosystems Model 392 DNA/RNA synthesizer, and may be labeled with a detectable marker such as a fluorescence, enzyme or radiolabeled markers including $^{32}$p and biotin, and the like. Combinations of two or more labelled probes corresponding to different regions of the nucleic acid also may be included in kits to allow for the detection and/or analysis of the gene by hybridization.

The present invention also provides a vector comprising nucleic acid encoding the human prostaglandin transporter (hPGT), as well as a cell stably transformed with the vector. The vector may be any plasmid, viral-derived nucleic acid, lytic bacteriophage derived from phage lambda, cosmid, filamentous single-stranded bacteriophage such as M13, and the like, for cloning nucleic acid or introducing the nucleic acid into a cell for expression. The cell may be eukaryotic or prokaryotic. Suitable host cells include but are not limited to bacterial cells such as *E. coli, Bacillus subtilis, Agrobacterium tumefaciens, Bacillus subtilis, Agrobacterium tumefaciens, Bacillus megaterium*, eukaryotic cells such as *Pichia pastoris, Chlamydomonas reinhardtii, Cryptococcus neoformans, Neurospora crassa, Podospora anserina, Saccharomyces cerevisiae, Saccharomyces pombe, Uncinula necator*, cultured insect cells, cultured chicken fibroblasts, cultured hamster cells, cultured human cells such as HT1080, MCF7, 143B and cultured mouse cells such as EL4 and NIH3T3 cells. Such expression systems may be used to produce a recombinant, human prostaglandin transporter (hPGT) by culturing a cell transformed with a vector comprising a nucleic acid human prostaglandin transporter (hPGT), and recovering the protein from the culture.

The present invention also provides a purified human prostaglandin transporter (hPGT). The protein may be the wild type protein or an analogue thereof, which includes functional variants of the wild type protein. The protein may be isolated from native cells or recombinantly produced. The present invention also provides antibodies immunoreactive with the human prostaglandin transporter (hPGT) (and analogues thereof). The antibodies may be polyclonal or monoclonal and are produced by standard techniques. The antibodies may be labeled with standard detectable markers (e.g. chemiluminescent detection systems and radioactive labels such as $^{125}$I). The antibodies also may be presented in kits with detectable labels and other reagents and buffers for such detection.

In addition, the present invention provides a method for evaluating the uptake of a selected prostaglandin by cells expressing nucleic acid encoding human prostaglandin transporter (hPGT). The method comprises the steps of: (a) expressing nucleic acid encoding human prostaglandin transporter (hPGT) in cells; (b) introducing the prostaglandin to the cells; and (c) evaluating the uptake of the prostaglandin by the cells. This method may be used to evaluate various prostaglandin analogues to determine their biological half-life, and design prostaglandin derivatives that are not transported by human prostaglandin transporter (hPGT) and thus might be cleared from the body more slowly than those that are transported by human prostaglandin transporter (hPGT). This assay may be performed as described below in the Experimental Details Section.

The present invention also provides a vector for use in preparing a non-human, transgenic animal comprising a nucleic acid encoding a mutant human prostaglandin transporter (hPGT) which is capable of introducing the nucleic acid in at least some embryonic cells to which the vector is introduced, an embryonic stem cell comprising a nucleic acid encoding a mutant human prostaglandin transporter (hPGT) which has been integrated into the cell following transduction with the vector above, as well as a non-human transgenic animal comprising nucleic acid encoding a mutant human prostaglandin transporter (hPGT).

The mutated nucleic acid may be integrated into the germ line of a non-human animal such as a mouse, rat, goat, sheep or other non-human species in order to obtain a transgenic animal model by methods known in the art (see Alberts, B., et al. *Molecular Biology of the Cell*, 2d. Garland Publ. Inc., New York and London, pp. 267–269 (1989)). For example, nucleic acid encoding the mutant human prostagland in transporter (hPGT) can be inserted into the genome of a replication-defective virus such as HSV or a retrovirus or transposen and the resultant construct injected into embryonic stem cells. Alternatively, the transgenic animal may be made by injecting nucleic acid into the male pronucleus of a fertilized egg of a nonhuman animal, transplanting the "transgenic embryo" into a pseudopregnant female and then analyzing offspring for the presence of the injected nucleic acid in their genome.

The present invention is described in the following Experimental Details Section, which is set forth to aid in an understanding of the invention, and should not be construed to limit in any way the invention as defined in the claims which follow thereafter.

Experimental Details Section

A. Materials and Methods

Human kidney cDNA library screening

A DNA fragment, obtained from the rat PGT cDNA by cutting with the restriction endonuclease Hinc1 followed by gel purification, was labeled by the random primer method (44) with [α-$^{32}$P] dCTP, and was used to probe a human kidney cDNA library in the phage vector λgt10 (_10$^8$pfu/ml. Clontech, Palo Alto, Calif.), generated by mixed deoxythymidine and random hexamer oligonucleotide primers. Following library plating and replica-transfer to Nytran Plus filters (Schleicher & Schuell, Keene, N.H.), filters were hybridized overnight at 40° C. with the $^{32}$P-labelled Hinc1 fragment in 5 ×SSC, 2% blocking reagent, 0.1% N-laurylsarcosine, and 0.02 % SDS (Genius System, Boehringer Mannheim, Indianapolis, Ind.).

Filters were washed as follows: twice with 1×SSC, 0.1% SDS at 40° C.; twice with 0.5×SSC, 0.1% SDS at 40° C.; twice with 0.1×SSC, 0.1% SDS at 40° C.; and twice with 1×SSC, 0.1% SDS at 50° C. Filters were exposed overnight to Kodak X-Omat AR film at −70° C. Positive plaques on duplicate filters were picked for secondary screening using the same hybridization and washing conditions. Of 800,000 colonies screened, seven positive clones were isolated and subcloned into the plasmid pSPORT-1 (Gibco, Gaitersburg, Md.).

DNA Sequencing, restriction analysis, and computer analysis.

All seven positive clones were subjected to restriction mapping. Using the dideoxy chain termination method (Sequenase version 2.0 DNA sequencing kit, USB, Cleveland, Ohio), all of both strands of clone 3 and parts of the other clones were sequenced by primer walking. In addition, parts of clones 5, 7, 9, and 10 were also sequenced. The data were aligned and analyzed by MacVector and GeneWorks software programs.

3' Rapid Amplification of cDNA Ends (RACE) by Polymerase Chain Reaction (PCR)

First strand cDNA was reverse-transcribed from human kidney poly-A (+) RNA (0.5 μg, Clontech) using a "Not1 primer-adapter" ("SuperScript Plasmid System", Gibco-BRL). The initial gene-specific 18-mer primer, generated from the region 3260–3277 of clone 3, and the Not1 primer-adapter were used in a first round of PCR. The initial denaturation at 94° for 1.5 minutes was followed by 20 cycles of denaturation at 94° for 30 sec, annealing at 50° for 30 sec, and extension at 72° for 1.5 min. A final extension at 72° was performed for 10 min. One μl of this product mixture was diluted into a second 50 μl reaction volume and nested PCR was performed with a second gene-specific 18-mer primer (region 3434–3451 of clone 3) and a 3' "anchor" primer (5'-TAGTTCTAGATCGCGAGCGG-3') generated from the "Not1 primer adapter". This second PCR was similar to the first except that the annealing temperature was 65° and the number of cycles was 35. The PCR product, which migrated at ~600 bp, was subcloned into the "TA" cloning vector (Stratagene, La Jolla, Calif.) and sequenced as above from the 3' end.

Transient expression in HeLa cells and transport assays.

The full-length clone 3 cDNA, subcloned in pSPORT1 with coding strand downstream of the T7 promoter, was transfected into cultured mammalian cells as follows. HeLa cells grown on 35 mm dishes were infected for 30 min with recombinant vaccinia vTF7-3 (45), the medium was changed, and the cells were then transfected by adding premixed cDNA (10 μg) and Lipofectin (20 μg, Gibco-BRL), after which there was an additional medium change at 3 hrs. The plasmid pBluescript KS was used as a negative control.

After 20 hrs, cells were washed, $^3$[H]-PG was added in Waymouth's solution, and timed uptake at 27° C. was determined. Uptake was stopped by one cold wash using Waymouth's with 5% bovine serum albumin and three cold washes with Waymouth's only. Cells were scraped and counted by liquid scintillation. On FIG. 2, data are the mean±SEM of 2 dishes from each of 2 separate monolayer transfections.

For determining PG uptakes (FIG. 2), the following $^3$[H]-PGs and final concentrations were used (New England Nuclear, Boston, Mass.): $PGE_2$: 0.7 nM (176 cpm/fmol); $PGE_1$: 0.6 nM (62 cpm/fmol); $PGD_2$: 0.9 nM (126 cpm/fmol); $PGF_{2\alpha}$: 0.6 nM (185 cpm/fmol); and $TxB_2$ 1.0 nM (114 cpm/fmol). In addition, the $PGI_2$ analog $^3$[H]-iloprost was used (Amersham, Arlington Heights, Ill.) at 7.9 nM (14 cpm/fmol).

Inhibition of tracer $PGE_2$ uptake

Tracer $PGE_2$ uptakes at 10 minutes (0.2 nM $^3$[H]-$PGE_2$) with or without various concentrations of unlabelled prostanoids (100–500 nM, Cayman Chemical, Ann Arbor, Mich.) or inhibitors (10–100 μM, Sigma, St. Louis) were determined in duplicate on a given transfection for one or two separate transfections. Because the substrate concentration was at least 500 times less than the concentration of the unlabeled prostanoid, we defined an apparent affinity constant, "$K_{1/2}$", from the equation:

$$K_{1/2}=[v/(v-v_i)][i]$$

where v=uptake without inhibitor, $v_i$=uptake with inhibitor, and [i]=inhibitor concentration (46).

Northern blot hybridization

Based on preliminary data indicating that a rat probe lacking much of the 3' untranslated region gave lower backgrounds, the rat PGT cDNA was shortened by restriction digesting it with BamH1 and re-ligating the remaining fragment, such that the resulting cDNA terminates at nucleotide 2055. An antisense digoxigenin-labeled RNA probe was generated from this clone using SP6 polymerase (Boehringer Mannheim) after linearizing with Sal1. A human PGT digoxigenin-labeled antisense probe was similarly generated from EcoR1-linearized clone 3 that had been previously shortened and re-ligated at the 3' end using Acc1. As a housekeeping probe, human β-actin cDNA ("Prime-It II", Stratagene) was labeled by the random primer method with $[\alpha-^{32}p]$ dCTP(3000 Ci/mmol, New England Nuclear).

Rat whole kidney total RNA, prepared by the acid guanidinium method (47), and 1 μg of human kidney poly-A+ RNA (Clontech, Palo Alto, Calif.) were separated by glyoxal denaturing agarose electrophoresis (44) and transferred to Hybond-N nylon membranes (Amersham). Separately, four multiple human tissue Northern blots were purchased from Clontech.

Blots probed with either the rat PGT or the clone 3 hPGT riboprobes were hybridized overnight at 65° in 5×SSC, 50% formamide, 2% blocking reagent, 0.1% N-laurylsarcosine, 0.02% SDS, and 0.01M EDTA (Genius System, Boehringer Mannheim). This was followed by sequential washes at 65°: twice in 1 X SSC, 0.1% SDS, 0.01M EDTA; twice in 0.5 X SSC, 0.1% SDS, 0.01M EDTA; and twice in 0.1 X SSC, 0.1% SDS, 0.01M EDTA. For the β-actin probe of the same membranes, hybridization was in 5×SSC, 2% blocking reagent, 0.1% N-laurylsarcosine, 0.02% SDS, and 0.01M EDTA overnight at 65° C. These blots were washed at 65°, twice in 1 X SSC, 0.1% SDS, 0.01M EDTA; twice in 0.5 X SSC, 0.1% SDS, 0.01M EDTA; and twice in 0.1 X SSC, 0.1% SDS, 0.01M EDTA.

Detection was performed using a horseradish peroxidase-coupled anti-digoxigenin antibody (Fab fragment) (Boehringer Mannheim). Signals were visualized by chemiluminescence autoradiography (ECL, Amersham).

B. Results

Figure 1:
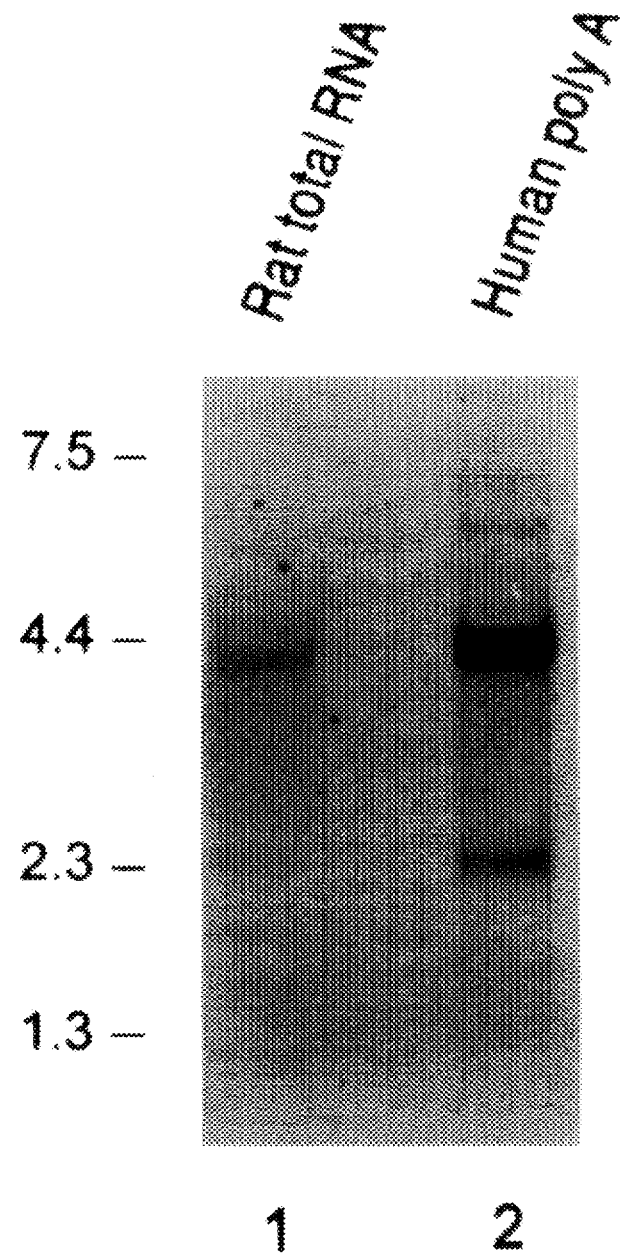
FIG. 1 represents the Northern blot hybridization of rat kidney total RNA (35 μg) and human kidney poly A+ RNA (1 μg) using a rat PGT anti-sense RNA probe. Hybridization and washing conditions are described in the Experimental Details Section below.

To search for human homologues of rat PGT, adult human kidney RNA was examined by Northern blotting it with a rat PGT antisense RNA probe. FIG. 1 shows that the rat probe revealed two bands of ~4.0 and 4.7 kb in total rat kidney RNA, as previously reported (36). When applied to human adult kidney poly A+ RNA at the same high stringency, the rat probe hybridized strongly to bands of 2.3 and 4.2 kb, and weakly to bands of 6.0 and 7.0 kb (FIG. 1). These results suggested that there was a human PGT homologue, with perhaps several PGT transcripts expressed in human kidney.

To understand the human homologue further, an adult human kidney cDNA library was screened with a $^{32}$-P-labeled rat PGT DNA probe. Seven hybridizing clones were isolated. After preliminary DNA sequencing and restriction mapping, six of the seven clones appeared to be related to each other and to rat PGT, and so were subjected to a more detailed analysis.

The longest clone isolated (#3) was 3.5 kb in length. Preliminary sequencing of this clone at the 5' end revealed similarity to rat PGT, including an ATG codon in good context for translation initiation (48). Before proceeding with sequencing, the function of clone 3 was tested using the vaccinia-T7 system (36, 45), on the assumption that mediation of PG transport would indicate that the clone did not contain splice artifacts causing frame shifts or premature stop codons.

Figure 2:
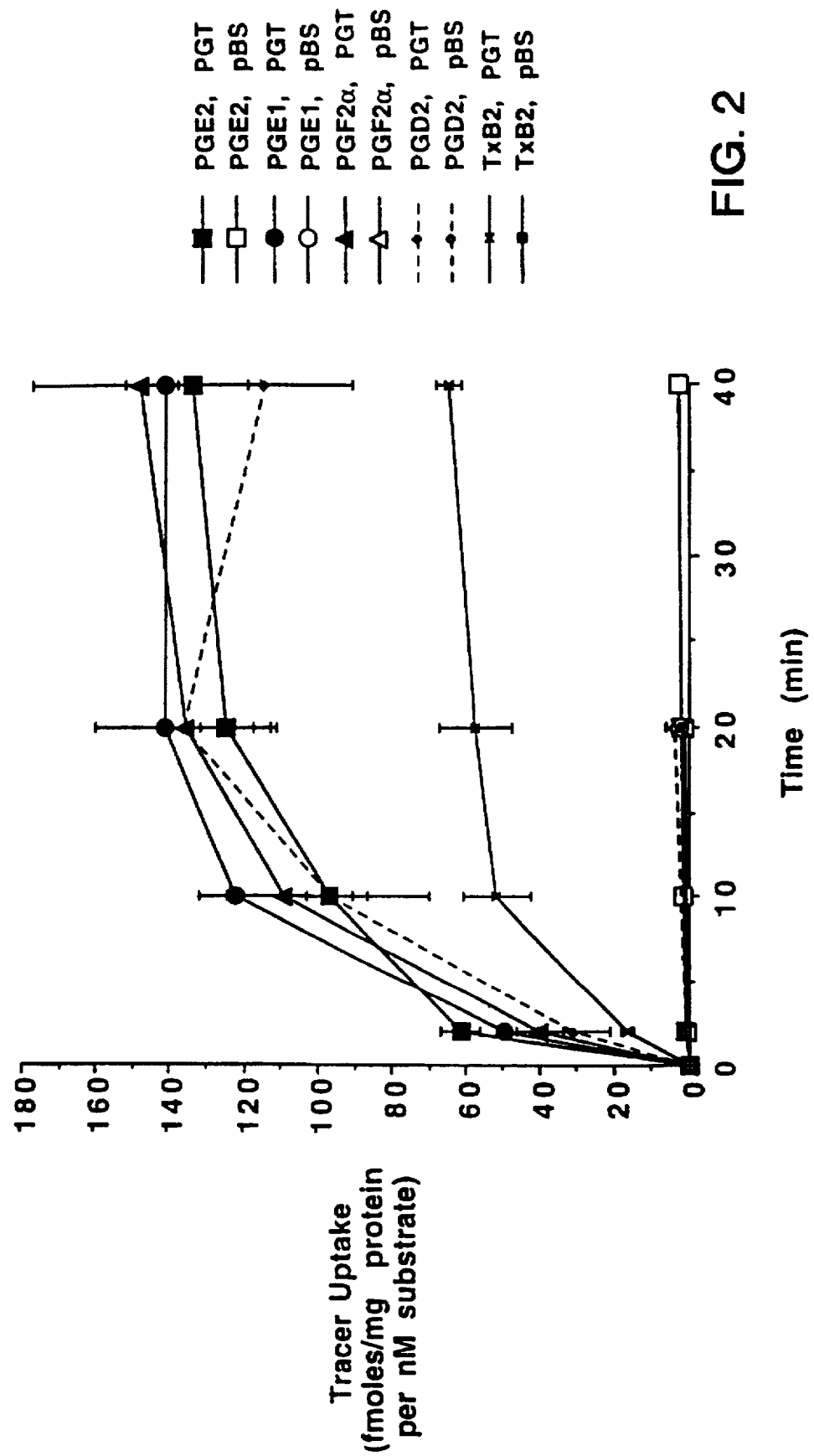
FIG. 2 represents the time-dependent uptake of tracer prostaglandins into HeLa cells expressing clone 3. "PGT", vector contained clone 3 cDNA; "pBS", vector was pBluescript control without any PGT sequence.

FIG. 2 shows that clone 3 catalyzed the rapid and time-dependent uptake of several PGs. The 2-minute rank-order of uptakes is $PGE_2>PGE_1>PGF_{2\alpha}>PGD_2>TxB_2$. By 10 and 20 minutes, there is essentially no difference between the transport rates of $PGE_2$, $PGE_1$, $PGF_{2\alpha}$, or $PGD_2$. In contrast, the prostacyclin analogue iloprost was not transported above baseline (data not shown). With the exception of the information on the transport of $PGD_2$, which is new to the present study, this rank order is very similar to that of rat PGT, as we recently reported (36). Because of the new finding here of $PGD_2$ transport by hPGT, the rat PGT was re-expressed in HeLa cells, and it was found that rat PGT also transports tracer $PGD_2$ at a rate equivalent to that of $PGE_2$ (data not shown). Taken together, the data of FIG. 2 indicate that clone 3 very likely represents a human homologue of rat PGT.

Table 1 presents results using three known PG transport inhibitors. Although furosemide was a moderately-potent inhibitor of hPGT, probenecid and indomethacin were much less effective. Table 1 also shows the inhibition of tracer $PGE_2$ by an excess of unlabeled prostanoids, assessed using clone 3. The apparent affinity constants ($K_{1/2}$, in nM) were: $PGE_2$=100, $PGD_2$=83, $PGF_{2\alpha}$=92, $PGE_1$=82, and $TxB_2$=182. (It should be noted that, because tracer uptake in the presence of unlabeled PGs was determined at 10 minutes and does not represent an "initial" value, "$K_{1/2}$" approximates, but does not equal, the Michaelis-Menten constant $K_m$).

Figure 3A:
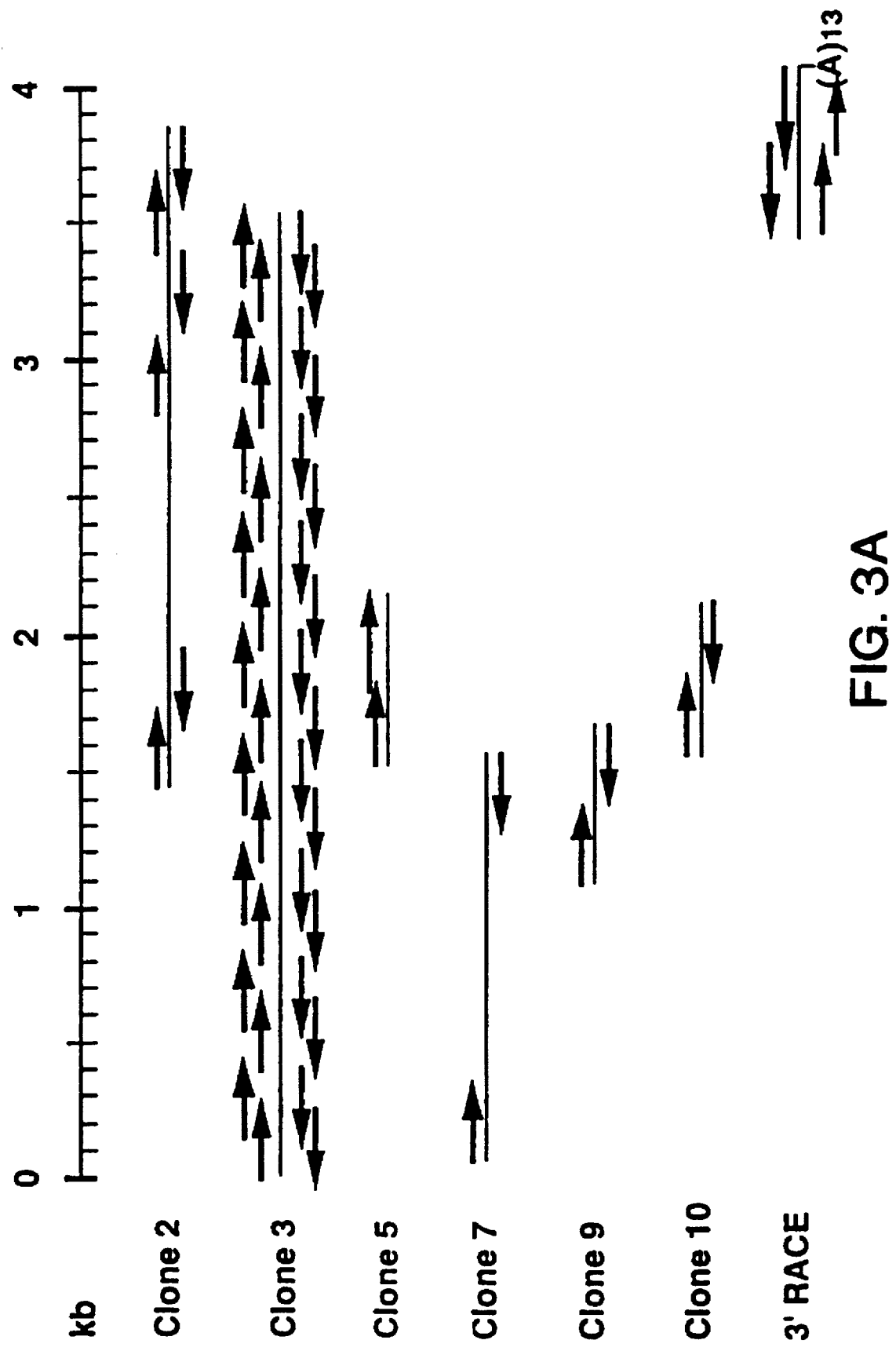
FIG. 3A represents the restriction and sequencing map of hPGT clones. Arrows indicate direction and length of dideoxy DNA sequencing runs.
Figure 4B:
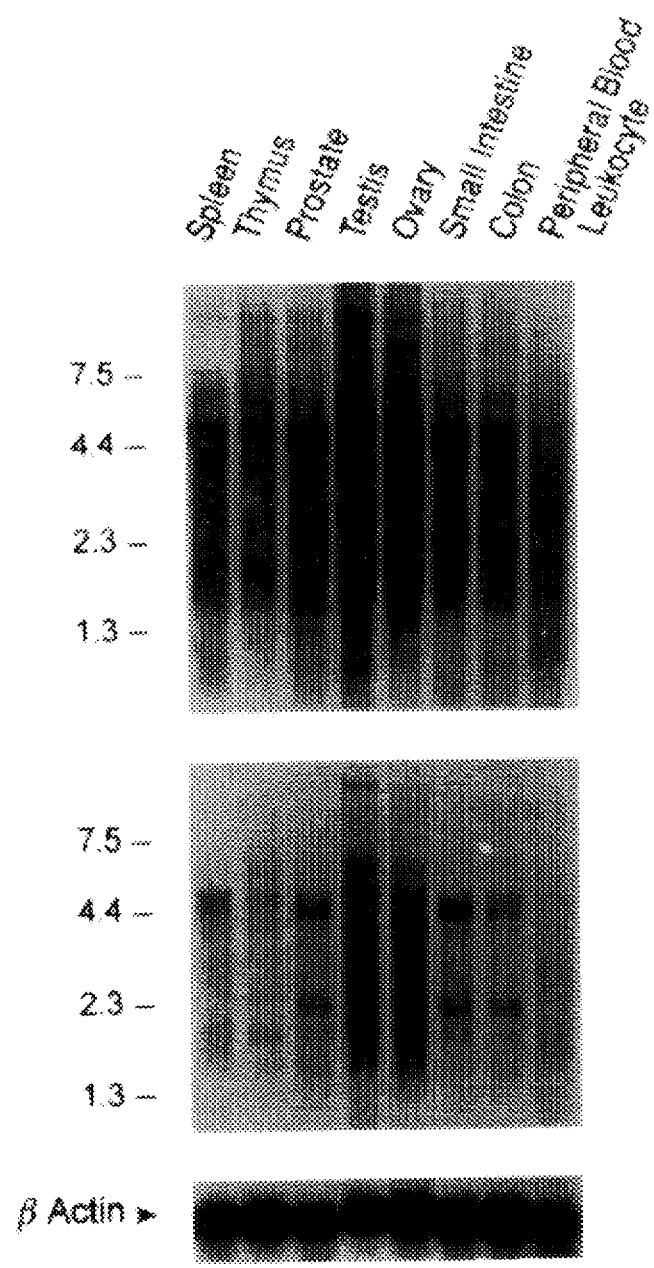

FIG. 3A shows the sequencing strategy and alignments of the six cDNA clones examined from the human kidney cDNA library. Clones #2 and #3 overlap and cover a total distance of 3.8 kb (FIG. 3A). The 3' end of clone 3 was used to generate two gene-specific primers for a 3' RACE strategy to clone the remaining 3' untranslated region. As described above, and as illustrated in FIG. 3a, a PCR product of 612 bp was amplified, cloned, and sequenced. This yielded 400 bp that overlap with the 3' end of clone 2, as well as 212 new nucleotides that terminate in a poly-A tail. The total length of the cDNA sequence assembled from clone 2, clone 3, and the 3' RACE sequence comprised 4046 base pairs, which is in reasonable agreement with the size of the major transcript in most tissues (~4.2 kb, FIGS. 4–6 below).

The consensus hPGT cDNA sequence, derived from all five clones, was 74% identical to that of the available comparable rat PGT cDNA sequence. There was also strong homology to several "expressed sequence tags" in the human database (accession numbers H63820, H63772, T85296, R25350, T85507, and R26541).

FIG. 3B compares the deduced amino acid sequences of hPGT and rat PGT starting at comparable ATG translation initiation codons (position 88 in the rat and 92 in the human). The predicted rat and human proteins are highly similar (82% identity). hPGT is predicted to have 12 membrane-spanning domains based on the Kyte-Doolittle hydropathy algorithm using a window of 13 residues (49). Glycosylation of hPGT could occur at any or all of three extracytoplasmic asparagine consensus sites (FIG. 3B).

In addition to its similarity to rat PGT, the hPGT deduced protein sequence is 32% identical to human "organic anion transporting polypeptide", or "oatp". Like PGT, oatp has been shown to be an organic anion transporter, primarily of bile salts and conjugated steroids (50, 51). It is therefore of interest that three charged residues in hPGT (E77, R561, and K614, see FIG. 3B), which lie within putative membrane spans, are highly conserved between hPGT, rat PGT, and oatp (50), suggesting that these amino acids may play an important role in anion transport.

The tissue distribution of hPGT expression in adult human tissues was examined by Northern blot analysis of poly A+ RNA (FIGS. 4A and B). A diversity of hybridizing transcripts was observed. The most strongly-hybridizing RNA bands were 1.8–2.0 kb in skeletal muscle, prostate, testis, ovary, small intestine, and colon; 2.5 to 2.9 kb in heart and skeletal muscle; 4.0 kb in ovary; 4.4 to 5.1 kb (often a doublet) in heart, whole brain, placenta, lung, liver, skeletal muscle, kidney, spleen, thymus, prostate, testis, ovary, small intestine, colon, and peripheral blood leukocytes; 8.8 kb in testis and colon; and 10.1 kb in testis. (The RNA derived from pancreas appeared to undergo some degradation, so statements about the exact PGT message in that organ remain limited).

Further examination of specific regions of the human brain by northern blotting revealed major transcripts of 2.1, 3.5, 4.8 and 7.5 kb in most regions, with an additional 10 kb band seen in the caudate nucleus (FIG. 5). Although it is possible that the 2.1 kb bands represents the riboprobe probe binding to 18S RNA, this seems unlikely because this blot utilized poly-A+ RNA, not total RNA, and because the carry-over of ribosomal RNA in the other blots was not seen. Moreover, the presence of strong bands of similar size in fetal lung, and in adult prostate, testis, ovary, small intestine, colon, and skeletal muscle argue that the 2.1 kb bands in brain derive from mRNA.

In human fetal tissues (FIG. 6), the RNA transcripts seen by northern blot hybridization were 2.1 kb in brain, lung, liver, and kidney; 2.5 kb in lung; 4.8 to 5.1 kb in brain, lung, liver, and kidney; 6.1 kb in liver; and 10 kb in lung and liver.

C. Discussion

We have cloned, sequenced, and heterologously-expressed a human homologue ("hPGT") of "PGT", a newly-recognized prostaglandin transporter that we previously identified in the rat (36). The hPGT nucleic acid and deduced amino acid sequences are similar to that of the rat transporter. In vitro expression of a full-length hPGT cDNA causes the transport of $PGE_1$, $PGE_2$, $PGD_2$ $PGF_{2\alpha}$, and to a lesser extent $TxB_2$. The mRNA expression for hPGT in native human tissues is very broad. Indeed, hPGT mRNA was seen in essentially every tissue or cell type examined, and there is a rich diversity of mRNA transcripts ranging from 1.8 to over 10 kb in length.

Although there is a substantial literature on carrier-mediated PG transport in other species (19–36), there is surprisingly little information about this phenomenon in humans, perhaps because of difficulty in obtaining tissue for such studies. $PGE_2$ has been shown to be transported by the isolated perfused human placental cotyledon (52) and by the isolated human amnion (35). Despite this paucity of direct information, the literature in animals, taken with the present functional profile and broad tissue expression pattern of hPGT, make it very likely that extensive carrier-mediated PG transport occurs in diverse human tissues.

We have postulated three possible roles for PGT (36). First, PGT might mediate the efflux of newly-synthesized PGs from cells. Although PGs apparently do gain access to the cytoplasmic compartment (37), it is unclear whether a carrier is necessary for their subsequent efflux into the extracytoplasmic space. Second, PGT might mediate epithelial PG transport. Vectorial PG transport occurs in many epithelia, including the liver, kidney, choroid plexus, anterior uvea, and uterus (22–24, 27, 33, 38, 39). The tissue distribution of PGT mRNA expression in the rat (36) suggested that its expression might be limited to epithelia, and therefore that epithelial transport of PGs may represent its primary function.

A third possible role of PGT is that of mediating PG clearance and degradation. After their release from cells, PGs and Txs bind to nearby surface receptors, where they signal a broad array of physiological functions. Because there is no enzymatic activity in the plasma capable of oxidizing $PGE_1$, $PGE_2$, or $PGF_{2\alpha}$ (38), these prostanoids could potentially bind to receptors at a substantial distance from their sight of release if they were not metabolized locally. Local clearance of $PGE_1$, $PGE_2$, and $PGF_{2\alpha}$ occurs in a single passage through any of several vascular beds, such as the lung (38, 40, 41). In contrast, prostacyclin ($PGI_2$) is not cleared, and thus circulates as a hormone (42, 43). The differing metabolism of these prostanoids appears to be due to differences in the selective uptake of some PGs into cells.

Of these three possibilities, we currently favor the "clearance" role for PGT, because 1) the substrate specificity of the cloned transporter is very similar to that reported previously for PG clearance in the isolated perfused rat lung preparation (20–22, 36); and 2) we have been unable to obtain PGT-mediated PG efflux using the Xenopus oocyte expression system (B. Chan and V. L. Schuster, unpublished observations).

As discussed above, it appears that PGT most likely plays a role in the uptake of newly-released PGs prior to intracellular oxidation. In this regard, the affinities of hPGT for its substrates are of interest. Despite the observation that hPGT and rat PGT both transport $TxB_2$ at a rate about half that of $PGE_2$ or $PGF_{2\alpha}$ (36) (FIG. 2), the $K_{1/2}$ of hPGT for this substrate is half that of the rat affinity constant (182 vs 423 nM, respectively, Table 1 and (36)), suggesting that PGT may play a more prominent role in thromboxane transport in the human than in the rat. Further studies will be required to address this possibility directly.

The apparent affinities ($K_{1/2}$) of hPGT for $PGE_2$ and $PGF_{2\alpha}$ are in the range of 80–100 nM. PG concentrations as presented to the transporter in tissues are probably at least this high. In human lung, for example, the $PGE_2$ concentration is about 25 ng/gram tissue, or ~70 nM; in human semen this value is ~25 µg/ml, or ~70 µM (53). On the other hand, plasma PGE and PGF concentrations in humans are about 0.25 ng/ml, or 0.7 nM (54). Assuming that hPGT is the mechanism for re-uptake of PGs after their release, this concentration would represent the residual from such a process.

Many transporters exist in families whose individual members recognize structurally-related, but distinct, substrates. It is therefore possible that transporters for other prostanoids exist. Indeed, PGT appears to be part of a gene family, the other currently-recognized member of which is "oatp" (36).

The presence of many different mRNA transcripts on high-stringency Northern blots suggests that several functionally distinct mRNAs may arise from a single hPGT gene. Such diverse hPGT transcripts could arise by alternative splicing and/or alternative promoters. At present, we have no definitive information with which to distinguish between these possibilities. However, we have recently isolated human genomic PGT clones (R. Lu and V. L. Schuster, unpublished observations), a step that should aid in addressing the origin of the diverse transcripts.

We also have no information at present as to whether transcripts that are either substantially larger or smaller than the ~4.0 kb cDNA encode functional transporters. It is of interest, however, that in neither the rat nor the human cDNA is the first methionine codon preceded by a stop codon (36). This raises the interesting possibility that the larger mRNA transcripts (e.g. the strong ~10 kb band in testis) might encode proteins that are extended at the amino-terminus relative to the present hPGT consensus cDNA. Confirmation of this hypothesis, as well as functional evaluation of any additional encoded proteins, must await isolation and characterization of additional cDNAs.

The presence of strongly-hybridizing hPGT mRNA transcripts in human heart and skeletal muscle stands in contrast to our findings in the rat, where there was no detectable expression, at least by northern blot analysis, in these two tissues (36). At present, we have no clear explanation for this difference other than species. The unequivocal expression of PGT mRNA in human heart and skeletal muscle argues against our previous conclusion that PGT is restricted to tissues containing epithelia (36). Because human hearts synthesize $PGE_2$, $PGF_{2\alpha}$, and 6-keto-$PGF_{1\alpha}$, especially in response to cold pressor testing (55–58), it is possible that PGT plays an as yet unidentified role in cardiac prostanoid metabolism.

The novel observation of $PGD_2$ transport by both rat and human PGT is of considerable physiological interest. $PGD_2$ has been implicated in several processes in the central nervous system (CNS), including the control of body temperature (59) and of olfactory function, hormone release, and pain perception (60). In addition, both $PGE_2$ and $PGD_2$ have been postulated to mediate central sleep-wake cycles (59, 61, 62). $PGE_2$ receptors are very widely-expressed in diverse structures of the rat brain (63). The equally-broad expression of hPGT mRNA in the human brain (FIG. 6), and the ability of cloned hPGT to transport $PGE_2$ and $PGD_2$ approximately equally well (FIG. 2), suggest that the transporter may play a role in the release, epithelial transport, and/or degradation of these prostanoids in the CNS. The present findings provide probes that should be useful in further studies on the CNS function of these eicosanoids.

There are other possible clinical implications of the present invention. First, circulating PG levels are elevated in several clinical circumstances, including bone marrow transplantation (64) and the "hyperprostaglandin syndrome". The latter is a Bartter-syndrome-like complex tubular disorder found in premature infants, characterized by increased systemic $PGE_2$ activity, fever, diarrhea, and osteopenia with hypercalciuria (65, 66). One hypothesis to explain these conditions would be a failure to clear circulating $PGE_2$ secondary to abnormal regulation or functional impairment of hPGT.

Second, various synthetic $PGE_1$ or $PGE_2$ analogs have been used to treat glaucoma (10, 11, 67) and impotence (68), to terminate pregnancy (12), and to provide gastric protection (13–15). The clinical use of these agents is predicated on certain assumptions about their pharmacokinetics, yet with few exceptions (69) detailed information about the clearance and metabolism of these agents in humans is lacking. Only recently, for example, was exogenous $PGE_1$ shown to be rapidly converted to circulating 13,14-dihydro-$PGE_1$, and 15-keto-$PGE_1$, in humans (70, 71). The role of hPGT, if any, in the clearance from the circulation of medicinal PGs can now be approached experimentally by expressing the transporter in vitro and evaluating its interactions with these agents. Moreover, in theory, at least, it should be possible to use the cDNA to design synthetic PGs that are not transported by hPGT, and thus might be cleared more slowly than those that are transported.

In summary, we have cloned, sequenced and heterologously-expressed a novel human PG transporter cDNA ("hPGT"), and have characterized the expression of hPGT mRNA in a large number of human tissues. The substrate specificity and broad tissue distribution suggest a role in the clearance and metabolism of several important endogenous prostanoids.

TABLE 1

Inhibition of hPGT-mediated tracer $PGE_2$ transport

| Inhibitor§ | 10 µM | 100 µM |
|---|---|---|
| Furosemide | 91.5 ± 3.3 | 63.3 ± 1.7 |
| Probenecid | 104 ± 5.2 | 92.8 ± 2.0 |
| Indomethacin | 114 ± 3.8 | 82.5 ± 1.0 |
| Unlabeled Prostanoid* | 100 nM | 500 nM |

TABLE 1-continued

| Inhibition of hPGT-mediated tracer PGE$_2$ transport | | |
|---|---|---|
| PGE$_1$ | 50.8 ± 3.4 | — |
| PGE$_2$ | 45.2 ± 1.4 | — |
| PGD$_2$ | 47.9 ± 0.9 | — |
| PGF$_{2\alpha}$ | 45.0 ± 1.3 | — |
| TXB$_2$ | — | 26.7 ± 0.1 |

§ Mean ± SEM from four separate determinations.
*Mean ± SEM from two separate determinations.

Uptakes were determined ± various inhibitors or unlabeled prostanoids. Results are shown as the percent of the control 10-min tracer PGE$_2$ uptake.

List of Cited References

1. Samuelsson, B. (ed). Prostaglandins and Related Compounds: Seventh International Conference, Florence, Italy. Advances in Prostaglandin, Thromboxane, and Leukotriene Research; Vol. 21A–B, Raven Press, New York, N.Y., 1990.

2. Murphy, R. C. and F. A. Fitzpatrick (eds). Arachidonate Related Lipid Mediators. Methods in Enzymology; Vol. 187, Academic Press, San Diego, 1990.

3. Bito, L. Z. and J. (Eds) Stjernschantz. The Ocular Effects of Prostaglandins and Other Eicosanoids. Progress in Clinical and Biological Research; Vol. 312, Alan R. Liss, New York, 1989.

4. Segal, M. B. (ed). Barriers and Fluids of the Eye and Brain. CRC Press, Boca Raton, Fla., 1992.

5. Levine, L. (ed). Arachidonate Metabolism in Immunologic Systems. Karger, N.Y., 1988.

6. Epstein, M. (ed). Prostaglandins and the kidney. American Journal of Medicine; Vol. 80, No. 1A, Technical Publishing, New York, N.Y., 1986.

7. Gugler, R. (ed). Prostaglandins in the Upper Gastrointestinal Tract: Focus on Misoprostol: Proceedings of the Second International Symposium. Digestive Diseases and Sciences; N.S. N. 31, No. 2, suppl., Plenum Press, N.Y., 1986.

8. Platelets, Prostaglandins, and the Cardiovascular System. Advances in Prostaglandin, Thromboxane, and Leukotriene Research; Vol. 13., Raven, N.Y., 1985.

9. Quiroga, J. and J. Prieto, Liver Cytoprotection by Prostaglandins, Pharmacol. Therap. 58:67–91 (1993).

10. Ziai, N., et al., The effects on Aqueous Dynamics of PhXA41, a New Prostaglandin F2 Alpha Analogue, After Topical Application in Normal and Ocular Hypertensive Human Eyes, Arch. Ophthalmol. 111:1351–1358 (1993).

11. Alm, A., et al., Intraocular Pressure-Reducing Effect of PhXA41 in Patients With Increased Eye Pressure. A One-Month Study, Ophthalmol. 100:1312–1316 (1993).

12. Ulmann, A., et al., Medical Termination of Early Pregnancy With Mifepristone (RU 486) Followed by a Prostaglandin Analogue. Study in 16,369 Women, Acta Obstet. Gynec. Scand. 71:278–283 (1992).

13. Konturek, S. J., et al., Effects of Nocloprost on Gastric Functions in Man, Scan. J. Gastro. 26:1145–1151 (1991).

14. Kobayashi, K., et al., Gastric Cytoprotection by Ornoprostil, a PGE1 Analogue, in Human Subjects, J. Clin. Gastro. 13 Suppl 1:S32–S36 (1991).

15. Bardhan, K. D., et al., Gastric Ulcer Healing: a Comparison of Enprostil Versus Ranitidine, J. Clin. Gastro. 13:157–162 (1991).

16. Roseman, T. J. and S. H. Yalkowsky, Physicochemical Properties of Prostaglandin F2 Alpha (Tromethamine Salt): Solubility Behavior, Surface Properties, and Ionization Constants, J. Pharm. Sci. 62:1680–1685 (1973).

17. Uekama, K., et al., Partition Behaviour and Ion Pair Formation of Some Prostaglandins, Chem. Pharm. Bull. 26:F58 (1978).

18. Bito, L. Z. and R. A. Baroody, Impermeability of Rabbit Erythrocytes to Prostaglandins, Am. J. Physiol. 229:1580–1584 (1975).

19. Eling, T. E. and M. W. Anderson, Studies on the Biosynthesis, Metabolism and Transport of Prostaglandins by the Lung, Agents Actions 6:543–546 (1976).

20. Anderson, M. W. and T. E. Eling, Prostaglandin Removal and Metabolism by Isolated Perfused Rat Lung, Prostaglandins 11:645–677 (1976).

21. Hawkins, H. J., et al., Uptake and Metabolism of Prostaglandins by Isolated Perfused Lung: Species Comparisons and the Role of Plasma Protein Binding, Prostaglandins 14:251–259 (1977).

22. Eling, T. E., et al., Structural Requirements for, and the Effects of Chemicals on, the Rat Pulmonary Inactivation of Prostaglandins, Prostaglandins 14:51–60 (1977).

23. Bito, L. Z. and E. V. Salvador, Effects of Anti-Inflammatory Agents and Some Other Drugs on Prostaglandin Biotransport, J. Pharmacol. Exp. Ther. 198:481–488 (1976).

24. Bito, L. Z., et al., Inhibition of In Vitro Concentrative Prostaglandin Accumulation by Prostaglandins, Prostaglandin Analogues and by Some Inhibitors of Organic Anion Transport, J. Physiol. (Lond) 256:257–271 (1976).

25. Bito, L. Z. and M. C. Wallenstein, Transport of Prostaglandins Across the Blood-Brain and Blood-Aqueous Barriers and the Physiological Significance of These Absorptive Transport Processes, Exp. Eye Res. 25 Suppl:229–243 (1977).

26. Hagen, A. A., et al., Levels and Disappearance of Prostaglandin F2alpha in Cerebral Spinal Fluid: a Clinical and Experimental Study, Stroke 8:672–675 (1977).

27. DiBenedetto, F. E. and L. Z. Bito, Transport of Prostaglandins and Other Eicosanoids by the Choroid Plexus: its Characterization and Physiological Significance, J. Neurochem. 46:1725–1731 (1986).

28. Suzuki, F., et al., Transport of Prostaglandin D2 into Brain, Brain Res. 385:321–328 (1986).

29. Bikhazi, A. B., et al., Transport of Prostaglandins Through Normal and Diabetic Rat Hepatocytes, J. Pharm. Sci. 72:296–299 (1983).

30. Bito, L. Z., Absorptive Transport of Prostaglandins From Intraocular Fluids to Blood: a Review of Recent Findings, Exp. Eye Res. 16:299–306 (1973).

31. Bito, L. Z., Saturable, Energy-Dependent, Transmembrane Transport of Prostaglandins Against Concentration Gradients, Nature (London) 256:134–136 (1975).

32. Jones, M. A. and M. J. Harper, Prostaglandin Accumulation by Isolated Uterine Endometrical Epithelial Cells From Six-Day Pregnant Rabbits, Biol. ReProd. 29:1201–1209 (1983).

33. Cao, Z. D., et al., Prostaglandin Translocation From the Lumen of the Rabbit Uterus In Vitro in elation to Day of Pregnancy or Pseudopregnancy, Biol. Reprod. 31:505–519 (1984).

34. Walenga, R. W., et al., Trans-Placental Transport and Metabolism of Carbacyclin by Perfused Human Placental In Vitro, Prostaglandins 37:121–134 (1989).

35. McCoshen, J. A., et al., The Role of Fetal Membranes in Regulating Production, Transport, and Metabolism of Prostaglandin E2 During Labor, *Am. J. Obstet. Gynecol.* 163:1632–1640 (1990).

36. Kanai, N., et al., Identification and Characterization of a Prostaglandin Transporter, *Science* 268:866–869 (1995).

37. Morita, I., et al., Expression-Activity Profiles of Cells Transfected With Prostaglandin Endoperoxide H Synthase Measured by Quantitative Fluorescence Microscopy, *Biochemistry* 34:7194–7199 (1995).

38. Ferreira, S. H. and J. R. Vane. , Prostaglandins: Their Disappearance From and Release into the Circulation, *Nature* 216:868–873 (1967).

39. Irish, J. M., Secretion of Prostaglandin E2 by Rabbit Proximal Tubules, *Am. J. Physiol.* 237:F268–273 (1979).

40. McGiff, J. C., et al., Selective Passage of Prostaglandins Across the Lung, *Nature* 223:742–745 (1969).

41. Piper, P. J., et al., Inactivation of Prostaglandins by the Lungs, *Nature* 225:600–604 (1970).

42. Moncada, S., et al., Prostacyclin is a Circulating Hormone, *Nature* 273:767–768 (1978).

43. Dusting, G. J., et al., Recirculation of Prostacyclin (PGI2) in the Dog, *Br. J. Pharmacol.* 64:315–320 (1978).

44. Sambrook, J., E. F. Fritsch, and T. Maniatis. 1989. Molecular Cloning. A Laboratory Manual. Cold Spring Harbor Laboratory Press, Cold Spring Harbor, N.Y.

45. Fuerst, T. R., et al., Eukaryotic Transient Expression System Based on Recombinant Vaccinia Virus That Synthesizes Bacteriophage T7 RNA Polymerase, *Proc. Natl. Acad. Sci. (USA)* 83:8122–8126 (1986).

46. Neame, K. D. and T. G. Richards. 1972. Elementary Kinetics of Membrane Carrier Transport. Wiley, N.Y.

47. Chomczynski, P. and N. Sacchi, Single-Step Method of RNA Isolation by Acid Guanidinium Thiocyanate-Phenol-Chloroform Extraction, *Anal. Biochem.* 162:156–159 (1987).

48. Kozak, M., An Analysis of Vertebrate mRNA Sequences: Intimations of Translational Control, *J. Cell Biol.* 115:887–903 (1991).

49. Kyte, J. and R. F. Doolittle, A Simple Method for Displaying the Hydropathic Character of a Protein, *J. Mol. Biol.* 157:105–132 (1982).

50. Jacquemin, E., et al., Expression Cloning of a Rat Liver $Na^+$-Independent Organic Anion Transporter, *Proc. Natl. Acad. Sci. USA* 91:133–137 (1994).

51. Kanai, N., et al., Estradiol 17-β D-Glucuronide is a High-Affinity Substrate for the Organic Anion Transporter "Oatp", *Am. J. Physiol. (Renal Fluid Electrolyte Physiol)* 270:F326–F331 (1996).

52. Glance, D. G., et al., Uptake, Transfer and Metabolism of Prostaglandin E2 in the Isolated Perfused Human Placental Cotyledon, *Prost. Leukotr. Med.* 21:1–14 (1986).

53. von Euler, U.S. and R. Eliasson. 1967. Prostaglandins. Academic Press, N.Y.

54. Zusman, R. M., et al., The Effect of Chronic Sodium Loading and Sodium Restriction on Plasma Prostaglandin A, E, and F Concentrations in Normal Humans, *J. Clin. Invest.* 52:1093–1098 (1973).

55. Neri Serneri, G. G., et al., Spontaneous and Cold Pressor Test-Induced Prostaglandin Biosynthesis by Human Heart, *Am. Heart J.* 110:50–55 (1985).

56. Neri Serneri, G. G., et al., Impaired Cardiac PGI2 and PGE2 Biosynthesis in Patients With Angina Pectoris, *Am. Heart J.* 112:472–478 (1986).

57. Nowak, J., et al., Cardiac Prostaglandin Formation in Man, *Adv. Myocardiology* 1:323–328 (1980).

58. Hirsh, P. D., et al., Release of Prostaglandins and Thromboxane into the Coronary Circulation in Patients with Ischemic Heart Disease, *N. Engl. J. Med.* 304:685–691 (1981).

59. Sri Kantha, S., et al., Effects of Prostaglandin D2, Lipoxins and Leukotrienes on Sleep and Brain Temperature of Rats, *Prostaqlandins Leukot. Essent. Fatty Acids* 51:87–93 (1994).

60. Ito, S., et al., Prostaglandin D2: a Biochemical Perspective, *Prostaclandins Leukot. Essent. Fatty Acids* 37:219–234 (1989).

61. Matsumura, H., et al., Prostaglandin D2-Sensitive, Sleep-Promoting Zone Defined in the Ventral Surface of the Rostral Basal Forebrain, *Proc. Natl. Acad. Sci. (USA)* 91:11998–12002 (1994).

62. Hayaishi, O., Molecular Mechanisms of Sleep-Wake Regulation: Roles of Prostaglandins D2 and E2, *FASEB J.* 5:2575–2581 (1991).

63. Matsumura, K., et al., Mapping of Prostaglandin E2 Binding Sites in Rat Brain Using Quantitative Autoradiography, *Brain Res.* 581:292–298 (1992).

64. Cayeux, S. J., et al., Elevated Plasma Prostaglandin E2 Levels Found in 14 Patients Undergoing Autologous Bone Marrow or Stem Cell Transplantation, *Bone Marrow Transpl.* 12:603–608 (1993).

65. Seyberth, H. W., et al., Congenital Hypokalemia With Hypercalciuria in Preterm Infants: a Hyperprostaglandinuric Tubular Syndrome Different From Bartter Syndrome, *J. Pediatr.* 107:694–701 (1985).

66. Seyberth, H. W., et al., Role of Prostaglandins in Hyperprostaglandin E Syndrome and in Selected Renal Tubular Disorders, *Pediatr. Nephrol.* 1:491–497 (1987).

67. Camras, C. B., et al., Intraocular Pressure Reduction With PhXA34, a New Prostaglandin Analogue, in Patients With Ocular Hypertension, *Arch. Ophthalmol.* 110:1733–1738 (1992).

68. Wolfson, B., et al., Intraurethral Prostaglandin E-2 Cream: a Possible Alternative Treatment for Erectile Dysfunction, *Urology* 42:73–75 (1993).

69. Karim, A., et al., Effects of Food and Antacid on Oral Absorption of Misoprostol, a Synthetic Prostaglandin El Analog, *J. Clin. Pharmacol.* 29:439–443 (1989).

70. Hesse, W. H., et al., Metabolism of Intravenously Administered Prostaglandin E1 in Patients With Peripheral Arterial Occlusive Disease, *Klin Wochenschr* 103:554–557 (1991).

71. Cawello, W., et al., Metabolism and Pharmacokinetics of Prostaglandin E1 Administered by Intravenous Infusion in Human Subjects, *Eur. J. Clin. Pharm.* 46:275–277 (1994).

All publications mentioned hereinabove are hereby incorporated by reference in their entirety.

While the foregoing invention has been described in detail for purposes of clarity and understanding, it will be appreciated by one skilled in the art from a reading of the disclosure that various changes in form and detail can be made without departing from the true scope of the invention in the appended claims.

What is claimed is:

1. A purified and isolated nucleic acid encoding human prostaglandin transporter (hPGT).

2. The nucleic acid of claim 1 which is genomic DNA, cDNA or RNA.

3. The nucleic acid of claim 1 encoding the amino acid sequence (SEQ. ID No.:2) contained in FIG. 3B.

4. The nucleic acid of claim 1 having the nucleotide sequence (SEQ. ID No.:1) contained in FIG. 7.

5. A probe comprising the nucleic acid of claim 1, or a complementary strand thereof.

6. The probe of claim 5 labeled with a detectable marker.

7. A vector comprising a nucleic acid encoding human prostaglandin transporter (hPGT).

8. The vector of claim 7 wherein the nucleic acid encodes the amino acid sequence (SEQ. ID No.:2) contained in FIG. 3B.

9. The vector of claim 7 wherein the nucleic acid encodes the nucleotide sequence (SEQ. ID No.:1) contained in FIG. 7.

10. A cell stably transformed with a vector comprising a nucleic acid encoding human prostaglandin transporter (hPGT).

11. The cell of claim 10 wherein the nucleic acid encodes the amino acid sequence (SEQ. ID No.:2) contained in FIG. 3B.

12. The cell of claim 10 wherein the nucleic acid has the nucleotide sequence (SEQ. ID No.:1) contained in FIG. 7.

13. A method for producing a recombinant, human prostaglandin transporter (hPGT) comprising culturing a cell transformed with a vector comprising a nucleic acid encoding human prostaglandin transporter (hPGT), and recovering human prostaglandin transporter (hPGT) from the culture.

14. The method of claim 13 wherein the nucleic acid encodes the amino acid sequence (SEQ. ID No.:2) contained in FIG. 3B.

15. The method of claim 13 wherein the nucleic acid has the nucleotide sequence (SEQ. ID No.:1) contained in FIG. 7.

16. A purified and isolated human prostaglandin transporter (hPGT).

17. The protein of claim 16 which is recombinantly produced.

18. The protein of claim 16 which has the amino acid sequence (SEQ. ID No.2) contained in FIG. 3B.

19. An antibody immunoreactive with the protein of claim 16, said antibody being labeled or unlabeled.

20. The antibody of claim 19 which is polyclonal.

21. The antibody of claim 19 which is monoclonal.

22. The labeled antibody of claim 19 that is labeled with a detectable marker.

\* \* \* \* \*